US007169903B2

(12) United States Patent
Schuman et al.

(10) Patent No.: US 7,169,903 B2
(45) Date of Patent: Jan. 30, 2007

(54) MULTIFUNCTIONAL MONOCLONAL ANTIBODIES DIRECTED TO PEPTIDOGLYCAN OF GRAM-POSITIVE BACTERIA

(75) Inventors: Richard F. Schuman, Gaithersburg, MD (US); John Fitzgerald Kokai-Kun, Frederick, MD (US); Simon J. Foster, Sheffield (GB); Jeffrey R. Stinson, Brookeville, MD (US); Gerald Walter Fischer, Bethesda, MD (US)

(73) Assignee: Biosynexus Incorporated, Gaithersburg, MD (US)

( * ) Notice: Subject to any disclaimer, the term of this patent is extended or adjusted under 35 U.S.C. 154(b) by 317 days.

(21) Appl. No.: 10/323,903

(22) Filed: Dec. 20, 2002

(65) Prior Publication Data

US 2003/0228322 A1    Dec. 11, 2003

Related U.S. Application Data

(60) Provisional application No. 60/343,444, filed on Dec. 21, 2001.

(51) Int. Cl.
- C12P 21/08    (2006.01)
- C07K 16/00    (2006.01)
- A61K 39/085   (2006.01)
- C07H 21/04    (2006.01)

(52) U.S. Cl. ............... 530/387.3; 530/388.1; 530/388.2; 424/192.1; 424/243.1; 435/69.7; 536/23.7; 536/23.5

(58) Field of Classification Search ............. 530/387.3, 530/388.1, 388.15, 388.2; 424/192.1, 243.1; 435/69.7; 536/23.7, 23.5
See application file for complete search history.

(56) References Cited

U.S. PATENT DOCUMENTS

| | | | |
|---|---|---|---|
| 4,596,769 A | 6/1986 | Shockman et al. | 435/7 |
| 5,571,511 A | 11/1996 | Fischer | 424/165.1 |
| 5,624,904 A | 4/1997 | Krieger et al. | 514/21 |
| 5,955,074 A | 9/1999 | Fischer | 424/130.1 |
| 6,610,293 B1 | 8/2003 | Fischer et al. | 424/133.1 |

OTHER PUBLICATIONS

Proc Natl Acad Sci USA 1982 vol. 79 p. 1979.*
Proc Natl Acad Sci USA 1988 vol. 85 3080-3084.*
Amit et el Science vol. 233 747-753 1986.*
Merkel, G.J. et al., "Characterization of a Monoclonal Antibody That Binds to an Epitope on Soluble Bacterial Peptidoglycan Fragments," *Clinical and Diagnostic Laboratory Immunology*, vol. 8, No. 3, pp. 647-651 (2001).
Wergeland et al., "Antibodies to Various Bacterial Cell Wall Peptidoglycans in Human and Rabbit Sera," *Journal of Clinical Microbiology*, 25(3):540-545 (1987).
Wergeland et al., "Antibodies to Staphylococcal Peptidoglycan and its Peptide Epitopes, Teichoic Acid, and Lipoteichoic Acid in Sera from Blood Donors and Patients with Staphylococcal infections," *Journal of Clinical Microbiology*, 27(6): 1286-1291 (1989).
U.S. Appl. No. 10/323,904, filed Dec. 20, 2002, Kokai-kun et al.
U.S. Appl. No. 09/097,055, filed Jun. 15, 1998, Fischer et al.
U.S. Appl. No. 60/341,806, filed Dec. 21, 2001, Kokai-kun et al.
Atrih et al., "Analysis of Peptidoglycan Structure from Vegetative Cells of *Bacillus subtilis* 168 and Role PBP 5 in Peptidoglycan Maturation," *Journal of Bacteriology*, 181:3956-3966 (1999).
Bartal et al., "Current Methods in Hybridoma Formation," (ed.) *Methods of Hybridoma Formation*, Humana Press, Clifton, New Jersey (1987).
Devereux et al., "A Comprehensive Set Of Sequence Analysis Programs For The VAX," *Nucl. Acids Res.*, 12:387-395 (1984).
Espersen et al., "Cross-Reactions Between *Staphylococcus* Epidermis and 23 Other Bacterial Species," *Acta Path. Microbial. Scand.*, Sect. B. 89: 253-260 (1981).
Fleer et al., "Septicemia Due to Coagulase-Negative Staphylococci In a Neonatal Intensive Care Unit: Clinical And Bacteriological Features And Contaminated Parenteral Fluids As A Source Of Sepsis," *Pediatr. Infect. Dis.*, 2: 426-431 (1983).
Foster, "Analysis of the Autolysins of *Bacillus subtilis* 168 during Vegetative Growth and Differentiation by Using Renaturin Polyacrylamide Gel Electrophoresis," *Journal of Bacteriology*, 174: 464-470 (1992).
Foster, "Molecular Analysis Of Three Major Wall-Associated Proteins Of *Bacillus subtilis* 168: Evidence For The Processing The Product Of A Gene Encoding A 258 kDa Precursor Two-Domain Ligand-Binding Protein," *Molecular Microbiology*, 8:299-310 (1993).
Fournier, "*Staphylococcu aureus*," *Vaccines and Immunotherapy*, Ch. 13, 166-177 (1991).
Green et al., "Antigen-Specific Human Monoclonal Antibodies From Mice Engineered With Human Ig Heavy And Light Chain YACs," *Nat Genet*, 7(1): 13-21 (1994).
Gribskov et al., "Sigma Factors From *E. coli*, *B. subtilis*, phage SP01, and phage T4 are Homologous Proteins," *Nucleic Acids Res.*, 14:6745-6763 (1986).
Hancock, "Bacterial Cell Surface Carbohydrates: Structure and Assembly," *Biochem. Soc. Trans.*, 25:183-187 (1997).
Jendeberg et al., "Engineering of $Fc_1$ and $Fc_3$ from Human Immunoglobulin G to Analyse Subclass Specificity for Staphyiococcal Protein A," *J. Immunol. Methods*, 201:25-34(1997).
Kantor et al, "Development Of The Antibody Repertoire As Revealed By Single-Cell PCR of FACS-sorted B-cell Subsets," *Ann N Y Acad Sci*, 764:224-227 (1995).

(Continued)

*Primary Examiner*—Lynette R. F. Smith
*Assistant Examiner*—Padma Baskar
(74) *Attorney, Agent, or Firm*—Lahive & Cockfield, LLP; Amy E. Mandragouras, Esq.; Megan E. Williams, Esq.

(57) ABSTRACT

The present invention encompasses protective monoclonal antibodies that bind to peptidoglycan of Gram-positive bacteria. The antibodies also bind to whole bacteria and enhance phagocytosis and killing of the bacteria in vitro and block nasal colonization by Gram-positive bacteria in vivo. The invention also provides human, humanized and chimeric antibodies. The invention also sets forth the heavy chain and light chain variable regions of an antibody within the invention.

12 Claims, 7 Drawing Sheets

OTHER PUBLICATIONS

Kengatharan et al., "Mechanism of Gram-Positve Shock: Identification of Peptidoglycan And Lipoteichoic Acid Moieties Essential In the Induction Of Nitric Oxide Synthase, Shock and Multiple Organ Failure," *Journal of Experimental Medicine*, 188: 305-315 (1998).

Kiser et al., "Development and Characterization of a *Staphylococcus aureus* Nasal Colonization Model in Mice," *Infection and Immunity*, 67: 5001-5006 (1999).

Lee, "The Prospects For Developing A Vaccine Against *Staphylococcus aureus*," *Trends in Micro.*, 4:162-66 (1996).

LoBuglio et al., "Mouse/Human Chimeric Monoclonal Antibody In Man: Kinetics And Immune Response," *P.N.A.S.*, 86:4220-4224 (1989).

Low et al, "Mimicking Somatic Hypermutation: Affinity Maturation of Antibodies Displayed on Bacteriophage Using a Bacterial Mutator Strain," *J Mol Biol*, 260(3):359-68 (1996).

Merkus, "Cyclodextrin in nasal drug delivery," *Advan. Drug Deliv. Rev*, 36:41-57 (1999).

Nakamura et al., "Uptake and Release of Budesonide from Mucoadhesive, pH-sensitive Copolymers and Their Application to Nasal Delivery," *J. Control. Release* 61:329-335. (1999).

Natsume, "Screening of Cationic Compounds as an Absorption Enhancer for Nasal Drug Delivery," *Int. J. Pharma*, 185:1-12 (1999).

Navarre et al., "Surface Proteins of Gram-Positive Bacteria and Mechanisms of Their Targeting to the Cell Wall Envelope," *Microbiology and Molecular Biology Reviews*, 63:174-229 (1999).

Needleman et al., A General Method Applicable to the Search for Similarities in the Amino Acid Sequence of Two Proteins, *J. Mol. Biol.*, 48;443-453 (1970).

Peterson et al., "Effect of Protein A on Staphylococcal Opsonization," *Infection and Immunity*. 15:760-764 (1977).

Peterson et al., "Influence of Encapsulation on Staphylococcal Opsonization and Phagocytosis by Human Polymorphonuclear Leukocytes," *Infection and Immunity*, 19:943-949 (1978).

Peterson et al., "The Key Role of Peptidoglycan in the Opsonization of *Staphylococcus aureus*," *The Journal of Clinical Investigation*, 61:597-609 (1978).

Quie et al., "Defective Phagocytosis of Staphylococci," *Annals New York Academy of Sciences*, 236:233-243 (1974).

Ramkissoon-Ganorkar et al., "Modulating Insulin-Release Profile From pH/thermosensivite Polymeric Beads Through Polymer Molecular Weight," *J. Contr. Release*, 59:287-298 (1999).

Romero-Vivas et al., Mortality Associated With Nosocomial Bacteremia Due To Methiciilin-Resistant *Staphylococcus aureus*, *Clin. Infect. Dis.*, 21:1417-23 (1995).

Salton, "The Bacterial Cell Envelope—A Historical Perspective, in J.-M. Ghuyson and R. Hakenbeck (ed.)," *Bacterial Cell Wall*, Elsevier Science BV, Amsterdam, 1-22 (1994).

Schwab et al. "Increased Adherence Of *Staphylococcus aureus* From Cystic Fibrosis Lungs To Airway Epithelial Cells," *Am. Rev. Respir. Dis.*, 148:365-369 (1993).

Schwartz et al., "Matrices For Detecting Distant Relationships," *Atlas of Protein Sequence and Structure National Biomedical Research Foundation*, 5 (suppl. 3):353-358 (1979).

Shulman et al., "A Better Cell Line for Making Hybridomas Secreting Specific Antibodies," *Nature*, 276:269-270 (1978).

Smith et al., "Comparison Of Biosequences," *Adv. Appl. Math*, 2:482-489 (1981).

Soto et al., "Bacitracin Versus Mupirocin For *Staphylococcus aureus* Nasal Colonization," *Infect. Cont. Hosp. Epidem*, 20: 351-353 (1999).

Suzuki et al., "Mucosal Drug Delivery Using Cellulose Derivative As A Functional Polymer," *J. Control. Release*, 62:101-107 (1999).

Timmerman et al., "Characterisation and Functional Aspects of Monoclonal Antibodies Specific for Surface Proteins of Coagulase-Negative Staphylococci," *J. Med. Micro.*, 35:65-71 (1991).

Tomasz, "The Staphylococcal Cell Wall, in V.A. Fischetti et al. (ed.)," *Gram-Positive Pathogens*, Ch. 36, 351-360 (2000).

Verbrugh et al., "Antibodies to Cell Wall Peptidoglycan of *Staphylococcus aureus* in Patients with Serious Staphylococcal Infections," *The Journal of Infectious Disease*, 144:1-9 (1981).

Verbrugh et al., "Opsonic Recognition of Staphylococci Mediated by Cell Wall Peptidoglycan: Antibody-Independent Activation of Human Complement and Opsonic Activity of Peptidoglycan Antibodies," *The Journal of Immunology* 124:1167-1173 (1980).

Wagner et al., "Antibodies Generated From Human Immunoglobufin Miniloci in Transgenic Mice," *Nucleic Acids Res*, 22(8): 1389-93 (1994).

Wagner et al., "The Diversity of Antigen-Specific Monoclonal Antibodies From Transgenic Mice Bearing Human Immunoglobulin Gene Miniloci," *Eur. J. Immunol.*, 24(11):2672-81 (1994).

Waldvogel, "*Staphylococcus aureus* (including Toxic Shock Syndrome), Mandrell, G.L. et. al. (ed.)," *Principles and Practices of Infectious Diseases, Third Edition*, Churchill Livingstone, 1489-1510 (1990).

Waldvogel, "*Staphylococcus aureus* (including Toxic Shock Syndrome), Mandrell, G.L. et. al. (ed.)," *Principles and Practice of Infectious Diseases, Fifth Edition*, Churchill Livingstone, 1760-1775 (2000).

Wang et al., "Human Immunoglobulin Variable Region Gene Analysis by Single Cell RT-PCR," *J. Immunol. Methods*, 244(1-2):217-25 (2000).

Winter et al., "Making Antibodies by Phage Display Technology," *Annu Rev Immunol.*, 12:433-55 (1994).

\* cited by examiner

FIGURE 2

A. Light Chain

```
 D  I  K  M  T  Q  S  P  L  T  L  S  V  T  I  G  Q  P  A  S
GATATTAAGATGACCCAGTCTCCACTCACTTTGTCGGTTACCATTGGACAACCAGCCTCC
CTATAATTCTACTGGGTCAGAGGTGAGTGAAACAGCCAATGGTAACCTGTTGGTCGGAGG

I  S  C  K  S  S  Q  S  L  L  D  S  D  G  K  T  Y  L  N  W
ATCTCTTGCAAGTCAAGTCAGAGCCTCTTAGATAGTGATGGAAAGACATATTTGAATTGG
TAGAGAACGTTCAGTTCAGTCTCGGAGAATCTATCACTACCTTTCTGTATAAACTTAACC

L  L  Q  R  P  G  Q  S  P  K  R  L  I  Y  L  V  S  K  L  D
TTGTTACAGCGGCCAGGCCAGTCTCCAAAGCGCCTAATCTATCTGGTGTCTAAACTGGAC
AACAATGTCGCCGGTCCGGTCAGAGGTTTCGCGGATTAGATAGACCACAGATTTGACCTG

S  G  V  P  D  R  F  A  G  S  G  S  G  T  D  F  T  L  K  I
TCTGGAGTCCCTGACAGGTTCGCTGGCAGTGGATCAGGGACAGATTTCACACTGAAAATC
AGACCTCAGGGACTGTCCAAGCGACCGTCACCTAGTCCCTGTCTAAAGTGTGACTTTTAG

S  R  V  E  A  E  D  L  G  V  Y  Y  C  W  Q  G  T  H  F  P
AGCAGAGTGGAGGCTGAGGATTTGGGAGTTTATTATTGCTGGCAAGGTACACATTTTCCT
TCGTCTCACCTCCGACTCCTAAACCCTCAAATAATAACGACCGTTCCATGTGTAAAAGGA

L  T  F  G  A  G  T  K  L  E  L  K                SEQ ID NO: 1
CTCACGTTCGGTGCTGGGACCAAGTTGGAACTGAAA               SEQ ID NO: 2
GAGTGCAAGCCACGACCCTGGTTCAACCTTGACTTT
```

B. Heavy Chain

```
 Q  V  Q  L  Q  Q  S  G  P  G  I  L  Q  P  S  Q  T  L  S  L
CAGGTTCAGCTGCAGCAGTCTGGCCCTGGGATATTGCAGCCCTCCCAGACCCTCAGTCTG
GTCCAAGTCGACGTCGTCAGACCGGGACCCTATAACGTCGGGAGGGTCTGGGAGTCAGAC

T  C  S  F  S  G  F  S  L  S  T  S  G  M  S  V  S  W  I  R
ACTTGTTCTTTCTCTGGGTTTTCACTGAGCACTTCTGGTATGAGTGTGAGCTGGATTCGT
TGAACAAGAAAGAGACCCAAAAGTGACTCGTGAAGACCATACTCACACTCGACCTAAGCA

Q  P  S  G  K  G  L  E  W  L  A  H  I  F  W  D  D  D  K  R
CAGCCTTCAGGAAAGGGTCTGGAGTGGCTGGCTCACATTTTCTGGGATGATGACAAGCGC
GTCGGAAGTCCTTTCCCAGACCTCACCGACCGAGTGTAAAAGACCCTACTACTGTTCGCG

Y  N  P  S  L  K  S  R  L  T  V  S  K  D  T  S  S  N  Q  V
TATAACCCATCCCTGAAGAGCCGACTCACAGTCTCCAAGGATACCTCCAGCAACCAGGTC
ATATTGGGTAGGGACTTCTCGGCTGAGTGTCAGAGGTTCCTATGGAGGTCGTTGGTCCAG

F  L  K  I  T  S  V  G  T  A  D  T  A  T  Y  Y  C  A  R  N
TTCCTCAAGATCACCAGTGTGGGCACTGCAGATACTGCCACATACTACTGTGCTCGAAAC
AAGGAGTTCTAGTGGTCACACCCGTGACGTCTATGACGGTGTATGATGACACGAGCTTTG

Y  D  Y  D  W  F  V  Y  W  G  Q  G  T  L  V  T  V  S  A    SEQ ID NO: 3
TATGATTACGACTGGTTTGTTTACTGGGGCCAAGGGACTCTGGTCACTGTCTCTGCA    SEQ ID NO: 4
ATACTAATGCTGACCAAACAAATGACCCCGGTTCCCTGAGACCAGTGACAGAGACGT
```

MULTIFUNCTIONAL MONOCLONAL ANTIBODIES DIRECTED TO PEPTIDOGLYCAN OF GRAM-POSITIVE BACTERIA

CROSS REFERENCE TO RELATED APPLICATIONS

This application is based on and claims the benefit of U.S. Provisional Application Ser. No. 60/343,444, filed Dec. 21, 2001. The entire disclosure of this provisional application is relied upon and incorporated by reference herein. This application relates to U.S. patent application Ser. No. 09/097,055, filed Jun. 15, 1998, which is specifically incorporated herein by reference, and to U.S. patent application Ser. No. 60/341,806, and the application entitled, *Methods for Blocking or Alleviating Staphylococcal Nasal Colonization by Intranasal Application of Monoclonal Antibodies*, filed herewith, and previously, on Dec. 20, 2001, and to U.S. Pat. Nos. 5,571,511 and 5,955,074, which are all specifically incorporated herein by reference.

DESCRIPTION OF THE INVENTION

1. Field of the Invention

This invention in the fields of immunology and infectious diseases relates to protective antibodies that are specific for Gram-positive bacteria, particularly to bacteria bearing exposed peptidoglycan on the surface. The invention includes monoclonal antibodies, as well as fragments, regions and derivatives thereof.

2. Introduction

Man has long battled infections caused by bacteria, particularly Gram-positive bacteria. The surface structures and cell wall of Gram-positive bacteria form a complex matrix that performs functions essential in bacteria and host interactions. The cell wall consists of a peptidoglycan macromolecule (repeating units of N-acetylglucosamine 2 and N-acetylmuramic acid) and attached accessory molecules including teichoic acids, lipoteichoic acids, and carbohydrates (see, e.g., (9) and (24)). In addition, there are many surface proteins anchored to the bacterial cell wall (see, e.g., (17)).

To protect itself against such bacteria, the body employs a variety of means. Mechanical barriers, such as the skin and mucous membranes, are the body's first line of defense. If a pathogen is able to circumvent these barriers and begin multiplying, then white blood cells called polymorphonuclear leukocytes, or PMNs, are the next mechanism that the body uses to respond to an infection. Finally, acquired immune mechanisms step in, wherein circulating antibodies and complement (soluble plasma proteins that can bind foreign targets non-specifically) bind to the invading pathogen and attract phagocytic cells, which in turn engulf and digest the pathogen. This latter mechanism is called phagocytosis, and the antibodies and complement that bind to the pathogen and promote phagocytosis are called opsonins. The enhancement of phagocytosis by opsonins is in turn called opsonization. Opsonization may rely on a combination of antibodies and complement (the "classical pathway"), or just on complement (the "alternative pathway"). The systems for opsonization and phagocytosis are significant because defective phagocytosis and killing of *staphylococci* (and other Gram-positive bacteria) leads to host invasion, infection and occasionally death.

Because of the prevalence of these bacteria on the skin and other surfaces, most mammals are exposed to Gram-positive bacteria. Thus, the polyclonal serum from any mammal, including humans, is likely to contain IgG that will bind to many different cell wall and surface components of Gram-positive bacteria. Such a collection of IgGs may serve to protect against Gram-positive bacteria because polyclonal IgG binding to many epitopes on surface antigens or cell wall molecules (such as peptidoglycan, teichoic acid, lipoteichoic acid, proteins and carbohydrates) may collectively be opsonic and promote phagocytosis of Gram-positive bacteria. Thus, the composite function of the antibodies in polyclonal serum may account for the serum's functional activity. However, such polyclonal IgG is clearly not always protective, as evidenced by the continued presence of infections due to such bacteria. To augment the level of antibodies against Gram-positive bacteria, clinicians administer vaccines based on these bacteria. However, many bacterial cell extracts that are used for immunization are not pure for one epitope or antigen, so the activity of the resulting antibodies may represent activities against several different cell wall components. This is particularly problematic if the cell wall is the antibody target, and the purity of the cell wall preparation cannot be verified.

Moreover, although perhaps protective in some individuals, polyclonal serum cannot be used to elucidate the functional role of an antibody to a single epitope because, by definition, a polyclonal serum contains many different antibodies, which bind to multiple antigens and epitopes. Each antibody may contribute to the composite functional activity. Consequently, the ability of antibodies directed against specific epitopes on the cell wall to act as opsonic factors for Gram-positive bacteria is not defined.

In addition, it is likely that some antibodies to an epitope will promote phagocytosis, while others will have different functions, such as blocking adherence of the bacteria to a cell. Thus, only monoclonal antibodies to specific epitopes can elucidate the potential functions of specific antibodies, such as enhancing phagocytosis, blocking bacterial adherence, or neutralizing toxic activities, and thereby form the basis of predictably protective treatments.

Moreover, until recently, determining the role of peptidoglycan or of antibodies to peptidoglycan was complicated by the impurity of peptidoglycan preparations. Teichoic acids and lipoteichoic acids are closely associated with cell wall peptidoglycan. In addition, for some bacteria, such as *S. epidermidis*, teichoic acid and lipoteichoic acid have the same glycerol phosphate backbone. These teichoic acid moieties can easily contaminate peptidoglycan preparations, which are prepared from cell wall extracts. Thus, the activity of serum raised against these preparations may not result from the activity of antibodies to peptidoglycan, but instead from the activity of antibodies to contaminates (see, e.g., (36)). Recently, we have developed monoclonal antibodies to LTA that have multiple functional activities, including opsonic activity, against Gram-positive bacteria. These antibodies can be used to confirm that peptidoglycan preparations are free of LTA contamination.

Furthermore, since peptidoglycan is ubiquitous in the bacterial world, highly specific opsonic or protective antibodies to peptidoglycan seem unlikely. In addition, the question about the role of protective antibody remained. Peterson and colleagues showed that normal human serum opsonized cell wall extracts and peptidoglycan (20). However, there were clearly many different antibodies to many different epitopes in the serum. At least three different antigenic sites have been distinguished on the peptidoglycan matrix. When Peterson and colleagues cleaved the peptidoglycan into small, soluble fragments with lysostaphin, the fragments were no longer opsonized in the presence of normal human serum. One explanation is that the smaller fragments could not support binding of a sufficient number of different antibodies, and that antibodies to a single epitope on peptidoglycan are not opsonic. Consequently, while peptidoglycan can activate the alternative pathway, which promotes opsonization and phagocytosis of *S. aureus* by complement alone, the role of antibodies and the classical pathway in opsonization and phagocytosis remained difficult to understand.

The role of antibodies in these processes was further in doubt when IgG deficient serum was found to be fully opsonic in studies by the same group. This result was consistent with studies by others that showed a normal level of killing by PMNs using serum that had been depleted of antibodies, and after blocking neutrophil IgG Fc receptors. An additional complication lies in the fact that many cell wall epitopes are deep under the surface and may be covered by proteins and capsular polysaccharide in live growing bacteria (18, 19).

Thus it was not known whether or not a monoclonal antibody to peptidoglycan that binds to a specific epitope could have functional activity without working in concert with other antibodies having other antigen or epitope specificities. It was also not known if an antibody with a single specificity could perform several functions important for host immunity and protection. Such monoclonal antibodies would be useful to prevent or treat Gram-positive infections, and the epitopes or antigens to which they bind would be useful as vaccines to induce protective immunity in a host.

SUMMARY OF THE INVENTION

This invention relates to therapeutic compositions comprising protective monoclonal antibodies (MAbs) to peptidoglycan (PepG) that enhance phagocytosis, block colonization and/or inhibit PepG induced- or facilitated-toxicity. As noted above, phagocytosis is important for effective immunity against Gram-positive bacteria. This invention provides protective opsonic MAbs to PepG that enhance phagocytosis and killing of Gram-positive bacteria and thus can block or treat systemic infections. Nasal colonization has been shown to be a primary reservoir for *staphylococci*, and a strong correlation has been demonstrated between staphylococcal nasal colonization and subsequent staphylococcal infections. This invention provides protective anti-PepG MAbs that block and/or alleviate nasal colonization by Gram-positive bacteria, such as *staphylococci*, and thereby reduce the incidence and/or severity of associated infections. Given intravenously, subcutaneously, intramuscularly, or through any other route of administration, protective anti-PepG MAbs may reduce the toxic effects of cell wall components. Thus, these therapeutic compositions both prevent and treat infections by Gram-positive bacteria.

The protective monoclonal antibodies of the invention include both IgG and IgM anti-PepG MAbs specific for PepG and include mouse, mouse/human chimeric, humanized or fully human MAbs specific for PepG. The protective monoclonal antibodies of this invention are directed to any of the multiple epitopes on PepG. They exhibit multiple binding characteristics and functional activities.

These protective monoclonal antibodies can be administered singly or in combination into the nares of normal or colonized human subjects or other mammals to block or alleviate bacterial colonization of the nasal mucosa and to thereby preclude systemic infections or reduce the spread of Gram-positive bacteria.

The invention also includes methods of using both single protective anti-PepG MAbs and combinations of MAbs to enhance phagocytosis, inhibit bacterial infection, which may result from colonization of the nasal mucosa and reduce toxic effects of PepG and other cell wall components or toxins.

In addition, PepG epitopes or antigens and peptides that mimic those epitopes and antigens would be useful as vaccines to elicit opsonic antibodies to Gram-positive bacteria.

BRIEF DESCRIPTION OF THE DRAWINGS

FIG. 2 shows the polypeptide and nucleic acid sequences of (A) the M130 antibody light chain variable region (SEQ ID NO: 1 and SEQ ID NO: 2) and (B) the M130 antibody heavy chain variable region (SEQ ID NO: 3 and SEQ ID NO: 4).

DETAILED DESCRIPTION OF THE INVENTION

Definitions

Figure 1:
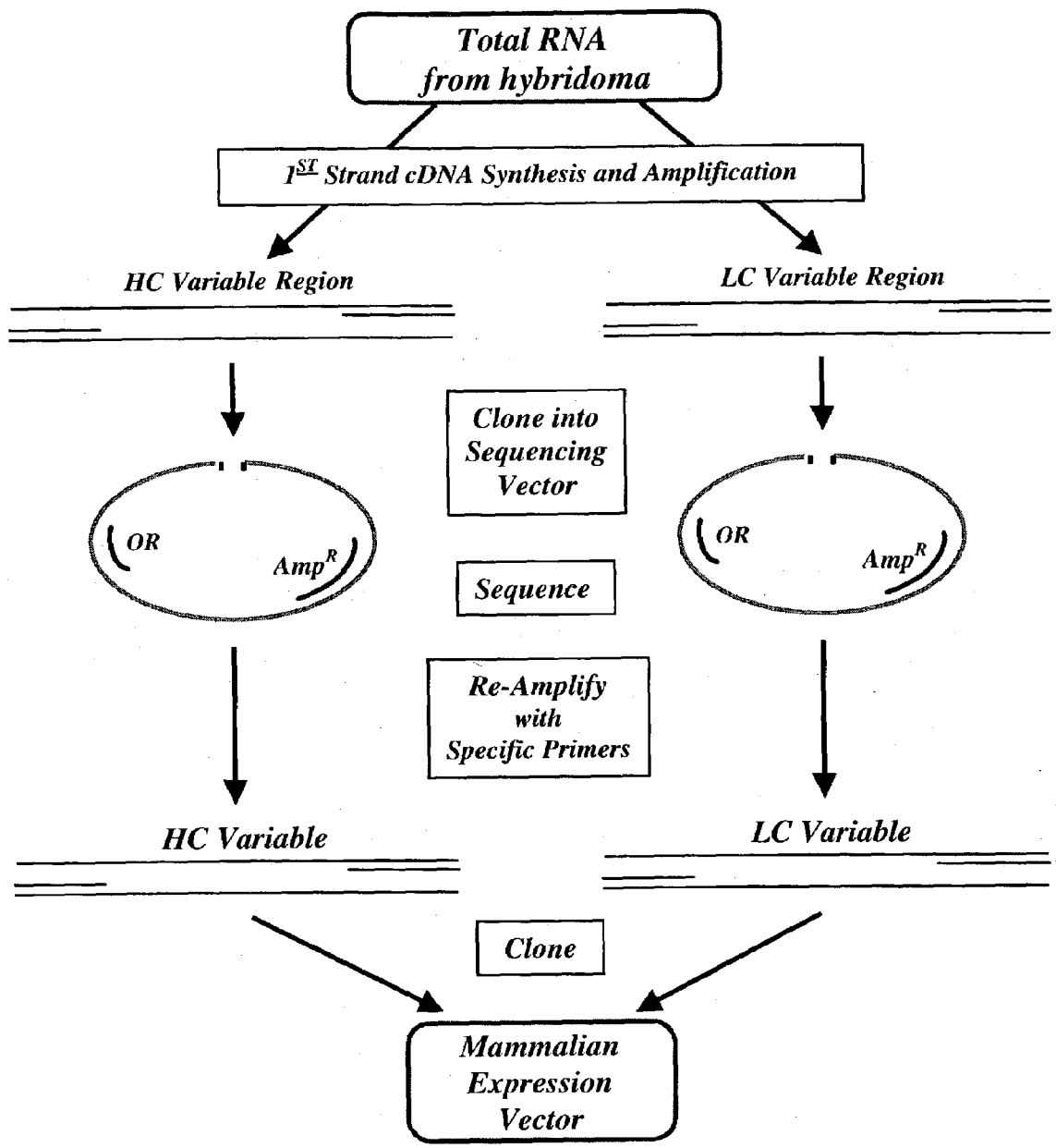
FIG. 1 shows the cDNA cloning strategy for the heavy chain and light chain variable regions of M130.

The term "antibody", as used herein, includes full-length antibodies and portions thereof. A full-length antibody has one pair or, more commonly, two pairs of polypeptide chains, each pair comprising a light and a heavy chain. Each heavy or light chain is divided into two regions, the variable region (which confers antigen recognition and binding) and the constant region (associated with localization and cellular interactions). Thus, a full-length antibody commonly contains two heavy chain constant regions (HC or CH), two heavy chain variable regions (HV or VH), two light chain constant regions (LC or CL), and two light chain variable regions (LV or VL) (FIG. 2). The light chains or chain may be either a lambda or a kappa chain. Thus, in an embodiment of the invention, the antibodies include at least one heavy chain variable region and one light chain variable region, such that the antibody binds antigen.

Another aspect of the invention involves the variable region that comprises alternating complementarity determining regions, or CDRs, and framework regions, or FRs. The CDRs are the sequences within the variable region that generally confer antigen specificity.

The invention also encompasses portions of antibodies which comprise sufficient variable region sequence to confer antigen binding. Portions of antibodies include, but are not limited to Fab, Fab', F(ab')$_2$, Fv, SFv, scFv (single-chain Fv), whether produced by proteolytic cleavage of intact antibodies, such as papain or pepsin cleavage, or by recombinant methods, in which the cDNAs for the intact heavy and light chains are manipulated to produce fragments of the heavy and light chains, either separately, or as part of the same polypeptide.

MAbs of the present invention encompass antibody sequence corresponding to human and non-human animal antibodies, and hybrids thereof. The term "chimeric antibody," as used herein, includes antibodies that have variable regions derived from an animal antibody, such as rat or mouse antibody, fused to another molecule, for example, a constant region domain derived from a human IgG, IgA, or IgM antibody.

One type of chimeric antibody, a "Humanized antibody" has the variable regions altered (through mutagenesis or CDR grafting) to match (as much as possible) the known sequence of human variable regions. CDR grafting involves grafting the CDRs from an antibody with desired specificity onto the FRs of a human antibody, thereby replacing much of the non-human sequence with human sequence. Humanized antibodies, therefore, more closely match (in amino acid sequence) the sequence of known human antibodies. By humanizing mouse monoclonal antibodies, the severity of the human anti-mouse antibody, or HAMA, response is diminished. The invention also includes fully human antibodies which would avoid the HAMA respose as much as possible.

The invention also encompasses "modified antibodies", which include, for example, the proteins or peptides encoded by truncated or modified antibody-encoding genes. Such proteins or peptides may function similarly to the antibodies of the invention. Other modifications, such as the addition of other sequences that may enhance an effector function, which includes the ability to block or alleviate nasal colonization by *staphylococci*, are also within the present invention. Such modifications include, for example, the addition of amino acids to the antibody's amino acid sequence, deletion of amino acids in the antibody's amino acid sequence, substitution of one or more amino acids in the antibody amino acid sequence with alternate amino acids, isotype switching, and class switching.

In certain embodiments, an antibody may be modified in its Fc region to prevent binding to bacterial proteins. The Fc region normally provides binding sites for accessory cells of the immune system. As the antibodies bind to bacteria, and coat them, these accessory cells recognize the coated bacteria and respond to infection. When a bacterial protein binds to the Fc region near the places where accessory cells bind, the normal function of these cells is inhibited. For example, Protein A, a bacterial protein found in the cell membrane of *S. aureus*, binds to the Fc region of IgG near accessory cell binding sites. In doing so, Protein A inhibits the function of these accessory cells, thus interfering with clearance of the bacterium. To circumvent this interference with the antibacterial immune response, the Fc portion of the antibody of the invention may be modified to prevent nonspecific binding of Protein A while retaining binding to accessory cells (see, e.g., (10)).

In light of these various forms, the antibodies of the invention include full-length antibodies, antibody portions, chimeric antibodies, humanized antibodies, fully human antibodies, and modified antibodies and will be referred to collectively as "MAbs" unless otherwise indicated.

The term "epitope", as used herein, refers to a region, or regions, of PepG that is bound by an antibody to PepG. The regions that are bound may or may not represent a contiguous portion of the molecule.

The term "antigen", as used herein, refers to a polypeptide sequence, a non-proteinaceous molecule, or any molecule that can be recognized by the immune system. An antigen may be a full-sized staphylococcal protein or molecule, or a fragment thereof, wherein the fragment is either produced from a recombinant cDNA encoding less than the full-length protein, or a fragment derived from the full-sized molecule or protein or a fragment thereof. Such fragments may be made by proteolysis. An antigen may also be a polypeptide sequence that encompasses an epitope of a staphylococcal protein, wherein the epitope may not be contiguous with the linear polypeptide sequence of the protein. The DNA sequence encoding an antigen may be identified, isolated, cloned, and transferred to a prokaryotic or eukaryotic cell for expression by procedures well-known in the art (25). An antigen may be 100% identical to a region of the staphylococcal molecule or protein amino acid sequence, or it may be at least 95% identical, or at least 90% identical, or at least 85% identical. An antigen may also have less than 100%, 95%, 90% or 85% identity with the staphylococcal molecule or protein amino acid sequence, provided that it still is able to elicit antibodies that bind to a native staphylococcal molecule or protein.

The percent identity of a peptide antigen can be determined, for example, by comparing the sequence of the target antigen or epitope to the analagous portion of staphylococcal sequence using the GAP computer program, version 6.0 described by Devereux et al. (Nucl. Acids Res. 12:387, 1984) and available from the University of Wisconsin Genetics Computer Group (UWGCG) (40). The GAP program utilizes the alignment method of Needleman and Wunsch (J. Mol. Biol. 48:443, 1970), as revised by Smith and Waterman (Adv. Appl. Math 2:482, 1981), and is applicable to determining the percent identity of protein or nucleotide sequences referenced herein (41, 42). The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353–358, 1979; (2) a penalty of 3.0 for each gap and an additional 0.10 penalty for each symbol in each gap; and (3) no penalty for end gaps (43, 44).

Alternatively, for simple comparisons over short regions up to 10 or 20 units, or regions of relatively high homology, for example between antibody sequences, or homologous portions thereof, the percent identity over a defined region of peptide or nucleotide sequence may by determined by dividing the number of matching amino acids or nucleotides by the total length of the aligned sequences, multiplied by 100%. Where an insertion or gap of one, two, or three amino acids occurs in a MAb chain, for example in or abutting a CDR, the insertion or gap is counted as single amino acid mismatch.

Antigens may be bacterial surface antigens and/or virulence and/or adherence antigens. Surface antigens are antigens that are accessible to an antibody when the antigen is in the configuration of the whole intact bacterium, i.e., the antigen is not inside the cell cytoplasm. Virulence antigens are antigens that are involved in the pathogenic process, causing disease in a host. Virulence antigens include, for example, LTA, peptidoglycan, toxins, fimbria, flagella, and adherence antigens. Adherence antigens mediate the ability of a staphylococcal bacterium to adhere to the surface of the nares. An antigen may be a non-proteinaceous component of *staphylococci* such as a carbohydrate or lipid. For example, peptidoglycan and lipoteichoic acid are two non-proteinaceous antigens found in the cell wall of *staphylococci*. Antigens may comprise or include fragments of non-proteinaceous molecules as long as they elicit an immune response.

As used herein, antigens include molecules that can elicit an antibody response to PepG. An antigen may be a PepG molecule, or a fragment thereof, wherein the fragment may be enzymatically, or otherwise, derived from the entire molecule or a fragment thereof. An antigen may also be a fragment of PepG that encompasses an epitope of PepG, wherein the epitope may not be contiguous with the macromolecular structure of the molecule. An antigen may be 100% identical to a region of PepG, or it may be 95% identical, or 90% identical, or 85% identical. An antigen may also have less identity with the PepG molecule, provided that it is able to elicit antibodies that bind to PepG. An antigen may also be an unrelated molecule, which, through some structural similarity, is able to elicit antibodies that bind to PepG. In certain embodiments of the invention, an antigen elicits antibodies that bind to PepG on the surface of bacteria. In certain embodiments, an antigen is a peptide that elicits antibodies that bind to PepG, and can be encoded by a cDNA. Procedures are generally described in *Molecular Cloning: A Laboratory Manual, 2$^{nd}$ Ed.*, which is herein incorporated by reference for any purpose (25).

Particular antigens of the invention include antigens that bind to any of the monoclonal antibodies produced by hybridomas 11-232.3, 11-248.2, 11-569.3, 11-232.3 IE9, 99-110FC12 IE4 (also referred to as MAb-11-232.3, MAb-11-248.2, MAb-11-569.3, MAb-11-232.3 IE9, and MAb-99-110FC12 IE4), A130, or M130, described herein.

An antibody is said to specifically bind to an antigen, epitope, or protein, if the antibody gives a signal by protein ELISA or other assay that is at least two fold, at least three fold, at least five fold, and at least ten fold greater than the background signal, i.e., at least two fold, at least three fold, at least five fold, or at least ten fold greater than the signal ascribed to non-specific binding. An antibody is said to specifically bind to a bacterium if the antibody gives a signal by, for example, methanol-fixed bacteria ELISA or live bacteria ELISA that is at least 1.5 fold, 2 fold, or 3 fold greater than the background signal.

"Enhanced phagocytosis", as used herein, means an increase in phagocytosis over a background level as assayed by the methods in this application, or another comparable assay. The level deemed valuable may well vary depending on the specific circumstances of the infection, including the type of bacteria and the severity of the infection. For example, enhanced phagocytic activity may be equal to or greater than 75%, 80%, 85%, 90%, 95%, or 100% over background phagocytosis. Enhanced phagocytosis may also be equal to or greater than 50%, 55%, 60%, 65%, or 70% over background phagocytosis. As used herein, opsonic activity may also be assessed by assays that measure neutrophil mediated opsonophagocytotic bactericidal activity.

The MAb's of the invention are useful for the prophylaxis and other treatment of systemic and local staphylococcal infections. In this respect, a MAb of the invention is said to "alleviate" staphylococcal nasal colonization if it is able to decrease the number of colonies in the nares of a mammal when the MAb is administered before, concurrently with, or after exposure to *staphylococci*, whether that exposure results from the intentional instillation of *staphylococcus* or from general exposure. For instance, in the nasal colonization animal model described below, a MAb or collection of MAbs is considered to alleviate colonization if the extent of colonization, or the number of bacterial colonies that can be grown from a sample of nasal tissue, is decreased after administering the MAb or collection of MAbs. A MAb or collection of MAbs alleviates colonization in the nasal colonization assays described herein when it reduces the number of colonies by at least 25%, at least 50%, at least 60%, at least 75%, at least 80%, or at least 90%. 100% alleviation may also be referred to as eradication.

A MAb is said to "block" staphylococcal colonization if it is able to prevent the nasal colonization of a human or non-human mammal when it is administered prior to, or concurrently with, exposure to *staphylococci*, whether by intentional instillation or otherwise into the nares. A MAb blocks colonization, as in the nasal colonization assay described herein, if no staphylococcal colonies can be grown from a sample of nasal tissue taken from a mammal treated with the MAb of the invention for an extended period such as 12 hours or longer or 24 hours or longer compared to control mammals. A MAb also blocks colonization in the nasal colonization assay described herein if it causes a reduction in the number of animals that are colonized relative to control animals. For instance, a MAb is considered to block colonization if the number of animals that are colonized after administering the material and the Gram-positive bacteria is reduced by at least 25%, at least 50%, and at least 75%, relative to control animals or if no colonies can be grown from a sample taken from a treated individual for an extended period such as 12 hours or 24 hours or longer.

In a clinical setting, the presence or absence of nasal colonization in a human patient is determined by culturing nasal swabs on an appropriate bacterial medium. These cultures are scored for the presence or absence of staphylococcal colonies. In this type of qualitative assay system, it may be difficult to distinguish between blocking and alleviation of staphylococcal colonization. Thus, for the purposes of qualitative assays, such as nasal swabs, a MAb "blocks" colonization if it prevents future colonization in human patients who show no signs of prior colonization for an extended period such as 12 hours or 24 hours or longer. A MAb "alleviates" colonization if it causes a discernable decrease in the number of positive cultures taken from a human patient who is already positive for *staphylococci* before the MAbs of the invention are administered.

Thus, the MAbs of the invention may be administered intranasally to block and/or alleviate staphylococcal nasal colonization. Administration (instillation) of an "effective amount" of the MAb results in a mammal that exhibits any of: 1) no nasal colonization by *staphylococci* for at least 12 hours after administration, 2) discernable, medically meaningful, or statistically significant decrease in the number of Gram-positive or staphylococcal colonies in the nares, or 3) a discernable, medically meaningful, or statistically significant decrease in the frequency of Gram-positive or staphylococcal cultures taken from the nares, or 4) a discernable, medically meaningful, or statistically significant decrease in the frequency of Gram-positive or staphylococcal infections.

"Instillation" encompasses any delivery system capable of providing a effective amount of a MAb to the mammalian nares.

A goal of the invention is to reduce the frequency of staphylococcal infections, including nosocomial infections. The administration of an effective amount includes that sufficient to demonstrate a discernable, medically meaningful, or statistically significant of decrease in the likelihood of staphylococcal infection involving a body site other than the nares, for example systemic infection, or infections at the site of trauma or surgery. Such demonstrations may encompass, for example, animal studies or clinical trials of patients at risk of infection by Gram-positive bacteria, including, but not limited to: premature infants, persons undergoing inpatient or outpatient surgery, burn victims, patients receiving indwelling catheters, stents, joint replacements and the like, geriatric patients, and those with genetically, chemically or virally suppressed immune systems.

As used herein, a "treatment" of a patient encompasses any administration of a composition of the invention that results in a "therapeutically beneficial outcome," hereby defined as: 1) any discernable, medically meaningful, or statistically significant reduction, amelioration, or alleviation of existing Gram-positive bacterial infection or colonization, or 2) any discernable, medically meaningful, or statistically significant blocking or prophylaxis against future bacterial challenge, infection, or colonization, or 3) any discernable, medically meaningful, or statistically significant reduction in the likelihood of nosocomial infection. Treatment thus encompasses a discernable, medically meaningful, or statistically significant reduction in the number of Gram-positive bacteria in a colonized or infected patient as well as a reduction in likelihood of future colonization or infection. As used herein, "colonized" refers to the subclinical presence of Gram-positive bacteria in patient, most particularly in the nares, whereas "infected" refers to clinical infection in any body site.

As used herein, "medically meaningful" encompasses any treatment that improves the condition of a patient; improves the prognosis for a patient; reduces morbidity or mortality of a patient; or reduces the incidence of morbidity or rates of mortality from the bacterial infections addressed herein, among a population of patients. The specific determination or identification of a "statistically significant" result will depend on the exact statistical test used. One of ordinary skill in the art can readily recognize a statistically significant result in the context of any statistical test employed, as determined by the parameters of the test itself. Examples of these well-known statistical tests include, but are not limited to, $X^2$ Test (Chi-Squared Test), Students t Test, F Test, M test, Fisher Exact Text, Binomial Exact Test, Poisson Exact Test, one way or two way repeated measures analysis of variance, and calculation of correlation efficient (Pearson and Spearman).

MAbs of the invention include "protective Mabs." Protective MAbs 1) exhibit strong binding to PepG, 2) enhance the opsonization and killing of Gram-positive bacteria (opsonophagocytic killing), and 3) reduce bacterial colonization. Such MAbs may also inhibit the toxicity that is induced or facilitated by PepG. In another embodiment, these protective MAbs encompass therapeutic compositions for the treatment of Gram-positive infections.

A vaccine is considered to confer a protective immune response if it stimulates the production of protective opsonic antibodies to Gram-positive bacteria. Production of protective opsonic antibodies may be measured by the presence of such antibodies in the serum of a test subject that has been administered the vaccine, relative to a control that has not received the vaccine. The presence of protective opsonic antibodies in the serum may be measured by the activity assays described herein, or by other equivalent assays. If an opsonophagocytic bactericidal assay is used, then killing by the test serum of at least 50% more bacteria, 75% more bacteria, and at least 100% more bacteria, relative to the control serum, is considered to be enhanced immunity.

EMBODIMENTS OF THE INVENTION

One aspect of the invention relates to protective anti-PepG MAbs that bind to whole bacteria. Bacteria include all Gram-positive bacteria, and in particular, *staphylococci* and streptococci. Since many epitopes of PepG may be unavailable on the surface of Gram-positive bacteria, this invention provides protective MAbs that bind to whole bacteria as well as to isolated PepG. By binding PepG, these protective MAbs may neutralize the toxic effects of these molecules.

Another aspect of the invention relates to protective MAbs that function as opsonins, binding in a manner that allows interaction with phagocytes, thereby promoting phagocytosis. Such protective MAbs may block or alleviate Gram-positive bacterial infections. These protective anti-PepG MAbs may be used either alone or in combination with MAbs of different specificity, for example, MAbs specific for LTA, to treat diseases caused by Gram-positive bacteria and/or other organisms. A further aspect of the invention is protective anti-PepG MAbs that may block or alleviate bacterial nasal colonization.

Particular embodiments of the invention include protective MAbs comprising the antigen-binding domains of the monoclonal antibodies MAb-11-232.3, MAb-11-248.2, MAb-11-569.3, MAb-11-232.3 IE9, MAb-99-110FC12 IE4, A130, or M130, described herein.

The invention also includes protective chimeric anti-PepG MAbs, in which the variable regions from a mouse monoclonal antibody are fused to human constant regions, and the chimeric antibody is produced in mammalian cell culture.

For example, a chimeric heavy chain may comprise the antigen binding region of the heavy chain variable region of a protective mouse anti-PepG MAb of the invention linked to at least a portion of a human heavy chain constant region. This chimeric heavy chain may be combined with a chimeric light chain that comprises the antigen binding region of the light chain variable region of a protective mouse anti-PepG MAb linked to at least a portion of a human light chain constant region.

In certain embodiments of the invention, a protective chimeric antibody is the human/mouse chimeric A130 antibody described herein. In another embodiment, a protective chimeric antibody comprises the antigen-binding domains of any of the monoclonal antibodies MAb-11-232.3, MAb-11-248.2, MAb-11-569.3, MAb-11-232.3 IE9, MAb-99-110FC12 IE4, A130, or M130, described herein.

Epitopes and antigens that are bound by protective anti-PepG monoclonal antibodies are also aspects of the invention. Further aspects of the invention include epitopes and antigens that elicit opsonic antibodies that bind to PepG of Gram-positive bacteria in vertebrates. These epitopes and antigens elicit protective opsonic antibodies when introduced into a human, a mouse, a rat, a rabbit, a dog, a cat, a cow, a sheep, a pig, a goat, or a chicken. Peptides that mimic those epitopes and antigens, and which can elicit opsonic antibodies to PepG of Gram-positive bacteria are also encompassed by the invention. These epitopes, antigens, peptides, and fragments of PepG may be used as vaccines to protect against, or alleviate, infections caused by Gram-positive bacteria.

The present invention also discloses therapeutic compositions comprising the protective anti-PepG MAbs of the invention, whether chimeric, humanized, or fully human, as well as fragments, regions, and derivatives thereof. These compositions may also include a pharmaceutically acceptable carrier. The therapeutic compositions of the invention may alternatively comprise the isolated antigen, epitope, or portions thereof, together with a pharmaceutically acceptable carrier.

In certain embodiments, a therapeutic composition of the invention includes, but is not limited to, a protective antibody comprising the antigen-binding domains of any of the monoclonal antibodies MAb-11-232.3, MAb-11-248.2, MAb-11-569.3, MAb-11-232.3 IE9, MAb-99-110FC12 IE4, A130, or M130, described herein.

Pharmaceutically acceptable carriers include, but are not limited to, sterile liquids, such as water, oils, including petroleum oil, animal oil, vegetable oil, peanut oil, soybean oil, mineral oil, sesame oil, and the like. Saline solutions, aqueous dextrose, and glycerol solutions can also be employed as liquid carriers. Suitable pharmaceutical carriers are described in Remington's Pharmaceutical Sciences, 18th Edition (8), which is herein incorporated by reference for any purpose.

Additionally, the invention may be practiced with various delivery vehicles and/or carriers. Such vehicles may increase the half-life of the Mabs in storage and upon administration including, but not limited to, application to mucus membranes, for example, upon inhalation or instillation into into the nares. These carriers comprise natural polymers, semi-synthetic polymers, synthetic polymers, liposomes, and semi-solid dosage forms (8, 16, 22, 26, 29, 30, 37). Natural polymers include, for example, proteins and polysaccharides. Semi-synthetic polymers are modified natural polymers such as chitosan, which is the deacetylated form of the natural polysaccharide, chitin. Synthetic polymers include, for example, polyphosphoesters, polyethylene glycol, poly (lactic acid), polystyrene sulfonate, and poly (lactide coglycolide). Semi-solid dosage forms include, for example, dendrimers, creams, ointments, gels, and lotions. These carriers can also be used to microencapsulate the MAbs or be covalently linked to the MAbs.

In one embodiment, the MAbs of the invention comprise, or are covalently or non-covalently bound to the outside of a carrier particle, which may be formulated as a powder, spray, aerosol, cream, gel, etc for application to the nares or infected area. In one embodiment, the MAbs are coated onto a carrier particle core in a dissolvable film, which may comprise a mucoadhesive. The carrier particle core may be inert, or dissolvable.

The invention further comprises any delivery system capable of providing a effective amount of a MAb to the mammalian nares or other infected area. Representative and non-limiting formats include drops, sprays, powders, aerosols, mists, catheters, tubes, syringes, applicators for creams, particulates, pellets, and the like. Also encompassed within the invention are kits comprising a composition containing one or more MAbs of the invention, in connection with an appropriate delivery device or applicator for the composition, for example: catheters, tubes, sprayers, syringes, atomizers, or other applicator for creams, particulates, pellets, powders, liquids, gels and the like.

Finally, the present invention provides methods for treating a patient infected with, or suspected of being infected with, a Gram-positive bacteria. The method comprises administering to a patient a therapeutically effective amount of a therapeutic composition comprising one or more of the protective anti-PepG MAbs (including monoclonal, chimeric, humanized, fully human, fragments, regions, and derivatives thereof) and a pharmaceutically acceptable carrier. A patient can be any human or non-human mammal in need of prophylaxis or other treatment. Representative patients include any mammal subject to *S. aureus, staphylococcal*, or Gram-positive infection or carriage, including humans and non-human animals such as mice, rats, rabbits, dogs, cats, pigs, sheep, goats, horses, primates, ruminants including beef and milk cattle, buffalo, camels, as well as fur-bearing animals, herd animals, laboratory, zoo, and farm animals, kenneled and stabled animals, domestic pets, and veterinary animals.

A therapeutically effective amount is an amount reasonably believed to provide measurable relief, assistance, prophylactive or preventive effect in the treatment of the infection. Such therapy as above or as described below may be primary or supplemental to additional treatment, such as antibiotic therapy for a Gram-positive bacterial infection, an infection caused by a different agent, or an unrelated disease. Combination therapy with other antibodies is expressly contemplated within the invention.

A further embodiment of the present invention is a method of blocking or alleviating such infections, comprising administering an effective amount of a therapeutic composition comprising the protective anti-PepG MAb (whether monoclonal or chimeric, humanized, or fully human, including fragments, regions, and derivatives thereof) and a pharmaceutically acceptable carrier.

An effective amount may be reasonably believed to provide some measure of blocking or alleviating infection by Gram-positive bacteria. Such therapy as above or as described below may be primary or supplemental to additional treatment, such as antibiotic therapy, for a staphylococcal infection, an infection caused by a different Gram-positive bacterial agent, or an unrelated disease. Indeed, combination therapy with other antibodies is expressly contemplated within the invention.

In another embodiment, a peptide that mimics any of the PepG epitopes would be useful to block binding of Gram-positive bacteria to epithelial cells and thereby inhibit colonization. For example, a therapeutic composition containing one or more such peptides may be administered intranasally to block or inhibit colonization, and therefore prevent or alleviate further infection.

Yet another embodiment of the present invention is a vaccine comprising one or more of the epitopes of the PepG antigen or one or more of the peptides that mimic a PepG epitope in a pharmaceutically acceptable carrier. Upon introduction into a host, the vaccine elicits an antibody broadly protective and opsonic against infection by Gram-positive bacteria. The vaccine may include the epitope, a peptide that mimics an epitope, any mixture of epitopes and peptides that mimic an epitope, the antigen, different antigens, or any combination of epitopes, peptides that mimic epitopes, and antigens. Standard techniques for immunization and analysis of the subsequent antibody response are found in: *Antibodies: A Laboratory Manual*, (Harlow & Lane eds., 1988), Cold Spring Harbor Laboratory Press; *Conjugate Vaccines*, (J. M. Cruse, R. E. Lewis, Jr. eds., 1989), Karger, Basel; U.S. Pat. Nos. 5,955,079, and 6,432,679 each of which is incorporated by reference.

The protective anti-PepG MAbs, vaccines, and therapeutic compositions of the invention are particularly beneficial for individuals known to be or suspected of being at risk of infection by Gram-positive bacteria, such as infant and elderly patients, immunocompromised patients, patients undergoing invasive procedures, patients undergoing chemotherapy, patients undergoing radiation therapy, and health care workers. This includes infants with immature immune systems, patients receiving body implants, such as valves, patients with indwelling catheters, patients preparing to undergo surgery involving breakage or damage of skin or mucosal tissue, certain health care workers, and patients expected to develop impaired immune systems from some form of therapy, such as chemotherapy or radiation therapy.

Among non-human patients, those at risk include zoo animals, herd animals, and animals maintained in close quarters.

The MAbs of the invention may be administered in conjunction with other antibiotic anti-staphylococcal drugs including antibiotics like mupirocin and bacitracin; anti-staphylococcal agents like lysostaphin, lysozyme, mutanolysin, and cellozyl muramidase; anti-bacterial peptides like nisin; and lantibiotics, or any other lanthione-containing molecule, such as nisin or subtilin.

In view of the disclosure provided, the administration of the MAbs of the invention is within the know-how and experience of one of skill in the art in light of the particular formulation and delivery method selected. In particular, the amount of MAbs required, combinations with appropriate carriers, the dosage schedule and amount may be varied within a wide range based on standard knowledge in the field without departing from the claimed invention. In one example, the MAbs of the invention may be given by intravenous drip or in discrete doses, doses may range from 1 to 4 or more times daily giving 0.1 to 20 mg per dose. In one embodiment, the amount of MAb administered would be 2–4 times per day at 0.1–3 mg per dose, a dose known to be effective with an inoculum of $10^8$ S. aureus bacteria, an amount of bacteria known to ensure 100% colonization in an animal model. Such a dosing regimen would be effective on patients either admitted to the hospital for surgical procedures, patients suffering from various conditions that predispose them to staphylococcal infections, convalescing patients, infants with immature immune systems, or prior to a patients' release from hospitals.

The protective anti-PepG antibodies, vaccines, and the therapeutic compositions of the invention may be administered by intravenous, intraperitoneal, intracorporeal injection, intra-articular, intraventricular, intrathecal, intramuscular, subcutaneous, intranasally, dermally, intradermally, intravaginally, orally, or by any other effective method of administration. The composition may also be given locally, such as by injection to the particular area infected, either intramuscularly or subcutaneously. Administration can comprise administering the therapeutic composition by swabbing, immersing, soaking, or wiping directly to a patient. The treatment can also be applied to objects to be placed within a patient, such as indwelling catheters, cardiac values, cerebrospinal fluid shunts, joint prostheses, other implants into the body, or any other objects, instruments, or appliances at risk of becoming infected with a Gram-positive bacteria, or at risk of introducing such an infection into a patient.

Particular aspects of the invention are now presented in the form of the following "Materials and Methods" as well as the specific Examples. Of course, these are included only for purposes of illustration and are not intended to limit the present invention.

MATERIALS AND METHODS

Bacteria

S. aureus, type 5, is deposited at the ATCC under Accession No. 49521.

S. aureus type 8, is deposited at the ATCC under Accession No. 12605.

S. epidermidis strain Hay, was deposited at the ATCC on Dec. 19, 1990 under Accession No. 55133.

S. hemolyticus is deposited at the ATCC under Accession No. 43252.

Hybridomas

Hybridoma 96-105CE11 IF6 (M110) was deposited at the ATCC on Jun. 13, 1997 under Accession No. HB-12368.

Hybridoma 99-110 FC12 IE4 was deposited at the ATCC on Sep. 21, 2000 under Patent Deposit PTA-2492.

Hybridoma 11-232.3 IE9 (M130) was deposited at the American Type Culture Collection (ATCC), located at P.O. Box 1549, Manassas, Virginia 20108, U.S.A., on Aug. 21, 2001 under the ATCC Number PTA-3659.

Isotype Determination Assay

Isotype was determined using a mouse immunoglobulin isotype kit obtained from Zymed Laboratories (Cat. No. 90-6550).

Binding Assays

In the binding assays of the invention, immunoglobulin is incubated with a preparation of whole cell staphylococci or with a preparation of bacterial cell wall components such as LTA or PepG. The binding assay may be an agglutination assay, a coagulation assay, a calorimetric assay, a fluorescent binding assay, or any other suitable binding assay that is known in the art. A particularly suitable assay is either an enzyme-linked immunosorbent assay (ELISA) or a radio-immunoassay (RIA). Binding is detected directly and can also be detected indirectly by using competitive or noncompetitive binding procedures known in the art.

The whole cell *staphylococcus* preparation, LTA preparation, PepG preparation, or a combination of those preparations, may be fixed using standard techniques to a suitable solid support, including, but not limited to, a plate, a well, a bead, a micro-bead, a paddle, a propeller, or a stick. Solid supports may be comprised of, for example, glass or plastic. In certain embodiments of the invention, the solid support is a microtiter plate.

Generally, a binding assay requires the following steps. First, the fixed preparation is incubated with an immunoglobulin source. In one embodiment of the assay, the immunoglobulin source is, for example, tissue culture supernatant or a biological sample such as ascites, plasma, serum, whole blood, or body tissue. In another embodiment, the immunoglobulin may be further isolated or purified from its source by means known in the art, and the purified or isolated immunoglobulin is subsequently used in the assay. The amount of binding is determined by comparing the binding in a test sample to the binding in a negative control. A negative control is defined as any sample that does not contain antigen-specific immunoglobulin. In the binding assay, a positive binding reaction results when the amount of binding observed for the test sample is greater than the amount of binding for a negative control. Positive binding may be determined from a single positive/negative binding reaction or from the average of a series of binding reactions. The series of binding reactions may include samples containing a measured amount of immunoglobulin that specifically binds to the fixed antigen, thereby creating a standard curve. This standard curve may be used to quantitate the amount of antigen-specific immunoglobulin in an unknown sample.

In an alternate embodiment of the assay, antibodies are fixed to a solid support and an unknown immunoglobulin sample is characterized by its ability to bind a bacterial preparation. The other aspects of the assays discussed above apply where appropriate.

The specific binding assays used in the Examples are set forth below:

Live Bacteria ELISA (LBE): The LBE assay was performed to measure the ability of antibodies to bind to live bacteria. Various types of bacteria may be used in this assay, including *S. aureus* type 5, type 5-USU, type 8, *S. epidermidis* strain Hay, and *S. hemolyticus*. Bacteria from an overnight plate culture was transferred to 35 ml of Tryptic Soy Broth (TSB) and grown with gentle shaking for 1.5–2.0 hours at 37° C. The bacteria were then pelleted by centrifugation at 1800–2000×g for 15 minutes at room temperature. The supernatant was removed and the bacteria were resuspended in 35–45 ml of phosphate buffered saline containing 0.1% bovine serum albumin (PBS/BSA). The bacteria were again pelleted by centrifugation, the supernatant discarded and the bacteria resuspended in PBS/BSA to a percent transmittance (% T) of 65%–70% at 650 nm. From this suspension the bacteria were further diluted 15-fold in sterile 0.9% sodium chloride (Sigma cat. no. S8776, or equivalent), and 100 µl of this suspension was added to replicate wells of a flat-bottomed, sterile 96-well plate.

Each antibody to be tested was diluted to the desired concentration in PBS/BSA containing 0.05% Tween-20 and horse radish peroxidase-conjugated Protein A (Protein A-HRP, Zymed Laboratories) at a 1:10000 dilution (PBS/BSA/Tween/Prot A-HRP). The Protein A-HRP was allowed to bind to the antibodies for 30–60 minutes at room temperature before use, thereby generating an antibody-Protein A-HRP complex to minimize the potential non-specific binding of the antibodies to the Protein A found on the surface of *S. aureus.*. Generally, several dilutions of test antibody were used in each assay. From each antibody dilution, 50 µl of the antibody-Protein A-HRP complex was added to replicate wells and the mixture of bacteria and antibody-Protein A-HRP complex was incubated at 37° C. for 30–60 minutes with gentle rotation (50–75 rpm) on an orbital shaker.

Following the incubation, the bacteria were pelleted in the plate by centrifugation at 1800–2000×g. The supernatant was carefully removed from the wells and 200 µl of PBS/BSA containing 0.05% Tween-20 (PBS/BSA/Tween) was added to all wells to dilute unbound reagents. The bacteria were again pelleted by centrifugation and the supernatant was removed. One hundred microliters of TMB substrate (BioFx, Inc. cat. no. TMBW-0100-01) was added to each well and the reactions were allowed to proceed for 15 minutes at room temperature. The reactions were stopped by adding 100 µl of TMB stop reagent (450 nm Stop Reagent; BioFx, Inc. catalog no. STPR-0100-01). The absorbance of each well was determined using a microplate reader fitted with a 450 nm filter.

In this assay, the intensity of the color development was directly proportional to the binding of the antibodies to the bacteria. Control wells contained bacteria and Protein A-HRP without antibody.

Immunoassay on Methanol-Fixed Bacteria: Heat-killed bacteria were suspended in sterile 0.9% sodium chloride (Sigma cat. no. S8776, or equivalent) at a % transmittance (% T) of 70–75% at 650 nm. Ten milliliters the bacterial suspension was diluted 15-fold in sterile 0.9% sodium chloride and then pelleted by centrifugation at 1800×g for 15 minutes at 10–15° C. The supernatant was discarded and the pellet was resuspended in 1500 ml of methanol (MeOH). One hundred microliters of the bacteria-MeOH suspension was distributed into each well of Nunc Maxisorp Stripwells (Nunc catalog no. 469949). The MeOH was allowed to evaporate, fixing the bacteria to the plastic wells. The bacteria-coated stripwells were stored in plastic bags in the dark at room temperature and used within 2 months of preparation.

For evaluation of antibodies, the bacteria-coated plates were washed four times with phosphate buffered saline containing 0.05% Tween-20 (PBS-T) as follows. Approximately 250 µl of PBS-T was added to each well. The buffer was removed by flicking the plate over the sink and the remaining buffer removed by inverting the plate and tapping it on absorbent paper. The antibody was diluted in PBS-T and then added to the wells. Supernatants, ascites, or purified antibodies were tested at the dilutions indicated in the Examples. Control wells received PBS-T alone. After addition of the antibody, the wells were incubated at room temperature for 30–60 minutes in a draft-free environment. The wells were again washed four times with PBS-T. Ninety-five microliters of detection antibody was then added to each well. The detection antibody was one of the following: rabbit anti-mouse IgG$_3$, rabbit anti-mouse IgM, or goat anti-human IgG (gamma-specific), all conjugated to horse radish peroxidase (HRP) and diluted 1:6000 in PBS-T (Zymed catalog numbers 61-0420, 61-6820 and 62-8420, respectively).

Following another 30–60 minute incubation at room temperature, the wells were washed four times with PBS-T and each well received 100 µl of TMB substrate solution (BioFx #TMBW-0100-01). Plates were incubated in the dark at room temperature for 15 minutes and the reactions were stopped by the addition of 100 µl of TMB stop solution (BioFx #STPR-0100-01). The absorbance of each well was measured at 450 nm using a Molecular Devices Vmax plate reader.

Immunoassay with Protein A: In order to evaluate the binding of the MAbs to *S. aureus*, the immunoassay procedure was modified for methanol-fixed bacteria, described above. Because *S. aureus* expresses Protein A on its surface, and Protein A binds strongly to the constant region of the heavy chains of gamma-globulins, it is possible that false positive results may be obtained from non-specific binding of the antibodies to Protein A. To overcome this difficulty, the immunoassay wells were coated with bacteria as described above, but prior to the addition of the antibodies to the bacteria-coated wells, the MAbs were incubated with a solution of recombinant Protein A conjugated to HRP (Zymed Laboratories Cat. No. 10-1123), diluted 1:8000 in PBS-T. The binding reaction was allowed to proceed for 30 minutes at room temperature. The wells were washed four times with PBS-T and 100 µl of the solution of each Protein A-HRP-MAb combination was added to the wells. The presence of the Protein A-HRP from the pretreatment blocked the MAbs from binding to the Protein A on the *S. aureus*. Furthermore, the binding of the Protein A-HRP to the constant region of the heavy chain did not interfere with the antibody binding site on the MAbs, thereby allowing evaluation of the MAbs on *S. aureus* and other bacteria.

The Protein A-HRP-MAb solutions were allowed to bind in the coated wells for 30–60 minutes at room temperature. The wells were then washed with PBS-T and TMB substrate solution was added and the assay completed as described above.

Immunoassay on LTA and PepG: The binding of the MAbs to LTA was measured by immunoassay on wells coated with *S. aureus* LTA (Sigma Cat. No. 2515). One hundred microliters of a 1 µg/ml LTA solution in PBS was distributed into replicate Nunc Maxisorp Stripwells and incubated overnight at room temperature. The unbound material was removed from the wells by washing four times with PBS-T. Antibody, diluted in PBS-T, was then added to the wells and the assay continued as described above for the Immunoassay on Methanol-Fixed Bacteria.

For immunoassays on PepG, Nunc Maxisorp Stripwell plates were coated with 100 µl of a 5 µg/ml solution of PepG (S. Foster; also can be prepared by the procedure set forth in Example 2) in 0.1 M carbonate buffer (pH 9.2–9.6) overnight at room temperature. Unbound antigen was removed from the plate by washing four times with PBS-T. Sample supernatants, ascites, or antibodies, diluted in PBS-T, were added to replicate wells. The plate was covered with a plate sealer and incubated for 30–60 minutes at room temperature in a draft-free environment. The plate was again washed with PBS-T, and 95 µl of gamma-specific Rabbit anti-Mouse IgG, conjugated to horseradish peroxidase (HRP) (Zymed Laboratories) was added to all wells. The plate was again covered and incubated in a draft-free environment for 30–60 minutes at room temperature. The plate was washed with PBS-T and 100 µl of TMB substrate solution was added to each well. After a 15 minute incubation at room temperature in the dark, 100 µl of TMB stop solution was added to all wells and the absorbance of each well was measured using a Molecular Devices $V_{max}$ plate reader with a 450 nm filter.

Activity Assays

Antibodies that bind to an antigen may not necessarily enhance opsonization or enhance protection from infection. Therefore, an opsonization assay was used to determine the functional activities of the antibodies.

An opsonization assay can be a calorimetric assay, a chemiluminescent assay, a fluorescent or radiolabel uptake assay, a cell-mediated bactericidal assay, or any other appropriate assay known in the art which measures the opsonic potential of a substance and thereby identifies reactive immunoglobulin. In an opsonization assay, an infectious agent, a eukaryotic cell, and the opsonizing substance to be tested, or an opsonizing substance plus a purported opsonizing enhancing substance, are incubated together.

In certain embodiments, the opsonization assay is a cell-mediated bactericidal assay. In this in vitro assay, an infectious agent such as a bacterium, a phagocytic cell, and an opsonizing substance, such as immunoglobulin, are incubated together. Any eukaryotic cell with phagocytic or binding ability may be used in a cell-mediated bactericidal assay. In certain embodiments, phagocytic cells are macrophages, monocytes, neutrophils, or any combination of these cells. Complement proteins may be included to promote opsonization by both the classical and alternate pathways.

The amount or number of infectious agents remaining after incubation determines the opsonic ability of an antibody. The fewer the number of infectious agents that remain after incubation, the greater the opsonic activity of the antibody tested. In a cell-mediated bactericidal assay, opsonic activity is measured by comparing the number of surviving bacteria between two similar assays, only one of which contains the antibody being tested. Alternatively, opsonic activity is determined by measuring the number of viable organisms before and after incubation with a sample antibody. A reduced number of bacteria after incubation in the presence of antibody indicates a positive opsonizing activity. In the cell-mediated bactericidal assay, positive opsonization is determined by culturing the incubation mixture under appropriate bacterial growth conditions. Any reduction in the number of viable bacteria comparing pre-incubation and post-incubation samples, or between samples that contain immunoglobulin and those that do not, is a positive reaction.

Neutraphil-Mediated Opsonophagocytic Bactericidal Assay: The assay was performed using neutrophils isolated from adult venous blood by sedimentation using PMN Separation Medium (Robbins Scientific catalog no. 1068-00-0). Forty microliters of antibody, serum, or other immunoglobulin source, was added at various dilutions to replicate wells of a round-bottom microtiter plate. Forty microliters of neutrophils (approximately $10^6$ cells per well) was then added to each well, followed immediately by approximately $3 \times 10^4$ mid-log phase bacteria (S. epidermidis strain Hay, ATCC 55133 or S. aureus type 5, ATCC 49521) in 10 µl Tryptic Soy Broth (Difco cat. no. 9063-74, or equivalent). Finally, 10 µl of immunoglobulin-depleted human serum was added as a source of active complement. (Immunoglobulins were removed from human serum complement by preincubating the serum with Protein G-agarose and Protein L-agarose before use in the assay. This depletion of immunoglobulins minimized the concentrations of anti-staphylococcal antibodies in the complement, thereby reducing bacterial killing caused by inherent antibodies in the complement solution.)

The plates were incubated at 37° C. with constant, vigorous shaking. Aliquots of 10 µl were taken from each well at zero time, when the sample antibody was first added, and after 2 hours of incubation. To determine the number of viable bacteria in each aliquot harvested from each sample well, each aliquot was diluted 20-fold in a solution of 0.1% BSA in water (to lyse the PMNs), mixed vigorously by rapid pipetting, and cultured on blood agar plates (Remel, cat. no. 01-202, or equivalent) overnight at 37° C. The opsonic activity was measured by comparing the number of bacterial colonies observed from the sample taken at two hours with the number of bacterial colonies observed from the sample taken at time zero. Colonies were enumerated using an IPI Minicount Colony Counter.

This cell-mediated bactericidal assay has been correlated with in vivo efficacy, as set forth in Examples 11 and 12 of U.S. Pat. No. 5,571,511.

Nasal Colonization Assay: The mouse nasal colonization model for S. aureus was based on the work of Kiser et al. (11). Briefly, streptomycin resistant S. aureus type 5 is grown on high salt Columbia agar (Difco) to promote capsule formation. The bacteria are washed with sterile saline (0.9% NaCl in water) to remove media components and resuspended at ~$10^8$ bacteria/animal dose in saline (0.9% NaCl in water) containing various concentrations and combinations of anti-staphylococcal or irrelevant control MAbs. Following one hour preincubation, the bacteria are pelleted and resuspended in a final volume of 10 µl per animal dose in either saline or saline containing antibody. Mice that have been maintained on streptomycin-containing water for 24 hours are sedated with anesthesia. Staphylococci are instilled into the nares of the mice by pipetting without contacting the nose.

After four to seven days, during which the animals are maintained on streptomycin-containing water, the animals are sacrificed and the noses removed surgically and dissected. Nasal tissue is vortexed vigorously in saline (0.9% NaCl in water) plus 0.5% Tween-20 to release adherent bacteria and the saline is plated on Columbia blood agar (Remel) and tryptic soy agar (Difco) containing streptomycin to determine colonization.

The invention, having been described above, may be better understood by reference to examples. The following examples are intended for illustration purposes only, and should not be construed as limiting the scope of the invention in any way.

EXAMPLES

Example 1

The Production of Hybridomas and Monoclonal Antibodies to *S. aureus* PepG Immunization of Mice To produce monoclonal antibodies directed against *S. aureus* PepG, immunizations were carried out using 5–6 week old female BALB/c mice, obtained from Harlan Sprague Dawley (Indianapolis, Ind.). The immunogen for the primary immunization was *S. aureus* PepG (gift from Roman Dziarski; PepG can also prepared as described in Example 2). Five microliters of PepG (7 mg/ml suspension) was mixed with 345 µl of PBS and 350 µl of RIBI adjuvant (RIBI Immunochemicals, Hamilton, N.H.). The resulting suspension contained 50 µg/ml of PepG. Each mouse was immunized with a subcutaneous (sc) dose of 0.1 ml (5 µg per mouse).

Approximately four weeks following the initial immunization, a booster immunization was given. PBS (873 µl) was mixed with 7.1 µl of PepG (7 mg/ml suspension) and 120 µl of Alhydrogel (Accurate Chemical and Scientific, Co., Westbury, N.Y.). Each mouse received an sc dose of 0.1 ml (5 µg of PepG per mouse).

After an additional eight weeks, the mice were immunized with a 50 µg/ml solution containing 50% Alum adjuvant (Pierce Cat. No.77161) in PBS (0.2 ml/mouse). Sera from the immunized mice were tested by ELISA as described above. As shown in Table 1, serum from mouse 8813 bound most strongly to PepG. This mouse was given a final, pre-fusion, intraperitoneal boost of 10 µg PepG in PBS three days prior to the generation of hybridomas.

TABLE 1

PepG ELISA of Sera from Mice Immunized with PepG

| Mouse ID | Serum Dilution | Serum Sample #1[a] | Serum Sample #2[b] |
|---|---|---|---|
| Buffer | 100 | 0.107 | 0.125 |
| 8810 | 100 | 0.341 | 0.339 |
| 8811 | 100 | 0.219 | 0.215 |
| 8812 | 100 | 0.267 | 0.249 |
| 8813 | 100 | 0.308 | 2.143 |
| 8814 | 100 | 0.223 | 0.296 |

[a]Sample was taken 9 weeks after the first immunization.
[b]Sample was taken 18 weeks after the first immunization.

Generation of Hybridomas

Hybridomas were prepared by the general methods of Shulman, Wilde and Kohler and Bartal, A. H. and Hirshaut (2, 28). Spleen cells from mouse 8813 were mixed with SP2/0 mouse myeloma cells (ATCC No. CRL1581) at a ratio of 10 spleen cells per SP2/0 cell, pelleted by centrifugation (400×g, 10 minutes at room temperature) and washed in serum free DMEM (Hyclone cat. no. SH30081.01, or equivalent). The supernatant was removed and fusion of the cell mixture was accomplished in a sterile 50 ml centrifuge conical by the addition of 1 ml of a 50% w/v solution of polyethylene glycol (PEG; mw 1500; Boehringer Mannheim cat. no. 783641) over a period of 60–90 seconds. Serum free medium was then added slowly in successive volumes of 1, 2, 4, 8, 16 and 19 ml. The hybridoma cell suspension was gently resuspended into the medium and the cells pelleted by centrifugation (500×g, 10 minutes at room temperature). The supernatant was removed and the cells resuspended in RPMI 1640, supplemented with 10% heat-inactivated fetal bovine serum, 0.05 mM hypoxanthine and 16 µM thymidine (HT medium; Life Technologies cat. no. 11067-030, or equivalent). One hundred microliters of the hybridoma suspension cells were plated into 96-well tissue culture plates. Eight wells (column 1 of plate A) received approximately $2.5 \times 10^4$ SP2/0 cells in 100 µl. The SP2/0 cells served as a control for killing by the selection medium added 24 hours later.

Twenty-four hours after preparation of the hybridomas, 100 µl of RPMI 1640, supplemented with 10% heat-inactivated fetal bovine serum, 0.1 mM hypoxanthine, 0.8 µM aminopterin and 32 µM thymidine (HAT medium, Life Technologies cat. no. 11067-030, or equivalent) was added to each well.

Ninety-six hours after the preparation of the hybridomas, the SP2/0 cells in plate A, column 1 were dead, indicating that the HAT selection medium had successfully killed the unfused SP2/0 cells. Twelve days after the preparation of the hybridomas, supernatants from all wells were tested by ELISA for the presence of antibodies that bind to PepG.

Based on the results of this preliminary assay, cells from 28 of the original 760 wells were transferred to a 24-well culture dishes. Four days later, supernatant from these cultures were retested by ELISA for the presence of antibodies that bind to PepG, using isotype-specific testing reagents. Briefly, supernatants from the cultures were added to 96-well plates coated with PepG and allowed to bind. To simultaneously detect binding of the antibodies to PepG, and the isotype of the antibodies, replicate wells were incubated with HRP-conjugated rabbit anti-mouse IgA, HRP-conjugated rabbit anti-mouse IgG, and HRP-conjugated rabbit anti-mouse IgM. The wells were then washed and developed by standard methods. As shown in Table 2, one of the cultures (99-110CF10) produced an IgG antibody and was passaged further. In addition, fifteen other cultures produced IgM antibodies and were also passaged further.

TABLE 2

PepG ELISA Assay of 99-110 Supernatants

| Supernatant ID | Supernatant Dilution | Isotype | Absorbance |
|---|---|---|---|
| Buffer | 2 | M | 0.077 |
| 99-110AD2 | 2 | M | 2.020 |
| 99-110AF5 | 2 | M | 1.741 |
| 99-110AA10 | 2 | M | 2.924 |
| 99-110BG8 | 2 | M | 3.702 |
| 99-110BA11 | 2 | M | 2.168 |
| 99-110CB2 | 2 | M | 3.747 |
| 99-110CG2 | 2 | M | 2.465 |
| 99-110DA4 | 2 | M | 2.606 |
| 99-110DF6 | 2 | M | 3.211 |
| 99-110DA10 | 2 | M | 3.570 |
| 99-110DA11 | 2 | M | 3.333 |
| 99-110EE4 | 2 | M | 1.131 |
| 99-110FC12 | 2 | M | 4.000 |
| 99-110GH4 | 2 | M | 4.000 |
| 99-110GC8 | 2 | M | 3.732 |
| 99-110CF10 | 2 | G | 0.102 |

Cultures 99-110CF10 and 99-110FC12 were subcloned by limiting dilution, as follows. Hybridomas were enumerated using a hemocytometer and adjusted to a concentration of 225 cells/ml. One ml of the cell solution was then mixed with 36 ml of RPMI 1640 medium, 7.5 ml of heat-inactivated fetal bovine serum, 0.5 ml of 10 mg/ml kanamycin solution (GIBCO BRL cat #15160-054), and 5 ml of Hybridoma Serum Free Medium (Life Technologies Cat. No.

12045-084). The resulting suspension contained 4.5 cells/ml. Two hundred microliters of this suspension was then added to each well of two 96-well culture dishes. As shown in Table 2 and Table 3, culture 99-110CF10 did not produce antibodies that bound to PepG. Subsequent subclones of culture 99-110CF10 likewise did not elicit PepG-specific antibodies.

TABLE 3

PepG ELISA of 99-110CF10 Clones

| Clone ID | Supernatant Dilution | Absorbance |
|---|---|---|
| Buffer | | 0.067 |
| CF10IC1 | 2 | 0.170 |
| CF10IE1 | 2 | 0.161 |
| CF10IG1 | 2 | 0.161 |
| CF10IH2 | 2 | 0.153 |
| CF10ID3 | 2 | 0.135 |
| CF10IC7 | 2 | 0.129 |
| CF10IF10 | 2 | 0.129 |

The clones from culture 99-110FC12, shown in Table 4, continued to produce IgM antibodies that bound to PepG. Thirty-two clones from 99-110FC12 were tested by ELISA on plates coated with PepG. Of these, 31 were strongly positive, producing absorbance values of 3.159 or greater. Four clones, designated 99-110FC12 IE4, ID3, IIH5 and IIC6 were expanded and cryopreserved. Clone IE4 was selected for additional analysis.

TABLE 4

PepG ELISA 99-110FC12 Clones

| Clone ID | Supernatant Dilution | Absorbance |
|---|---|---|
| Buffer | | 0.039 |
| FC121F1 | 2 | 3.495 |
| FC12IE2 | 2 | 2.651 |
| FC12ID3 | 2 | 4.000 |
| FC12IF3 | 2 | 3.159 |
| FC12IG3 | 2 | 3.811 |
| FC12IE4 | 2 | 4.000 |
| FC12ID6 | 2 | 3.937 |
| FC12IE6 | 2 | 4.000 |
| FC12IC7 | 2 | 0.074 |
| FC12IH7 | 2 | 4.000 |
| FC12IF8 | 2 | 4.000 |
| FC12IG8 | 2 | 3.533 |
| FC12IF11 | 2 | 4.000 |
| FC12IG11 | 2 | 4.000 |
| FC12IA12 | 2 | 4.000 |
| FC12IIB2 | 2 | 3.456 |
| FC12IID2 | 2 | 4.000 |
| FC12IIG2 | 2 | 4.000 |
| FC12IIF3 | 2 | 4.000 |
| FC12IIG3 | 2 | 3.379 |
| FC12IIB4 | 2 | 4.000 |
| FC12IIG4 | 2 | 4.000 |
| FC12IIA5 | 2 | 3.887 |
| FC12IIH5 | 2 | 4.000 |
| FC12IIC6 | 2 | 4.000 |
| FC12IIE6 | 2 | 3.756 |
| FC12IIG6 | 2 | 4.000 |
| FC12IIA10 | 2 | 3.844 |
| FC12IIC10 | 2 | 3.450 |
| FC12IIH10 | 2 | 3.980 |
| FC12IIH11 | 2 | 4.000 |

Clone 99-110FC12 IE4 was grown in an Integra Biosystems Culture system, designed to produce high quantities of immunoglobulin in culture supernatants. Supernatant from the IE4 clone was tested by ELISA on wells coated with methanol-fixed *S. epidermidis* strain Hay, PepG, and LTA. As shown in Table 5, the antibody bound strongly to *S. aureus* PepG, but not to the methanol-fixed bacteria, or to *S. aureus* LTA.

TABLE 5

Binding of 99-110FC12 IE4 supernatant by ELISA

| Supernatant Dilution | On *S. aureus* PepG | On *S. aureus* LTA | On methanol-Fixed *S. epi* Strain Hay |
|---|---|---|---|
| 10 | 3.789 | 0.051 | 0.078 |
| 30 | 3.983 | 0.052 | 0.075 |
| 90 | 3.974 | 0.048 | 0.073 |
| 270 | 4.00 | 0.047 | 0.069 |
| 810 | 3.858 | 0.044 | 0.065 |
| PBS-T | 0.044 | 0.045 | 0.056 |

Example 2

Production of Hybridomas and Monoclonal Antibodies to *B. subtilis* PepG Purification of Peptidoglycan

*Bacillus subtilis* HR (gift of Howard Roger, University of Kent, UK) vegetative cell walls were made as previously described under stringent conditions, using lipopolysaccharide-free materials (6, 38), which are herein incorporated for any purpose). Proteins were removed from the peptidoglycan by treatment with pronase, and teichoic acid and other attached polymers were removed by treatment with HF (48% v/v) for 24 h at 4° C. The insoluble peptidoglycan was pelleted by centrifugation (13,000 g, 5 min, 4° C.) and resuspended in distilled water to 2 mg/ml PepG. This step was repeated once. The peptidoglycan was then pelleted and resuspended in 50 mM Tris HCl pH7.5 to 2 mg/ml PepG, and this step was repeated once. Finally, the peptidoglycan was pelleted and resuspended in distilled water to 2 mg/ml PepG three more times. The peptidoglycan was resuspended at about 10 mg/ml in distilled water and stored at −20° C.

PepG preparations were analyzed as previously described by sodium dodecyl sulfate-polyacrylamide gel electrophoresis (SDS-PAGE), which revealed no evidence of contaminating protein (39). The purity of the peptidoglycan was further verified by amino acid analysis of hydrolyzed PepG, which gave only the expected amino acids, and by reverse phase chromatography analysis of enzymatically digested material, both assays performed as previously described (1). This level of purity had previously not been ensured during the production of anti-peptidoglycan antibodies.

Preparation of Muropeptide Conjugate for Immunization

Peptidoglycan conjugate was made as per the manufacturers protocol for the Imject SuperCarrier EDC System for Peptides (Pierce, cat. no. 77152).

Muropeptides were made by Cellosyl digestion. Cellosyl is a muramidase that cleaves the bond between N-acetylmuramic acid and N-acetylglucosamine in the glycan backbone of PepG. Complete cellosyl digestion of PepG results in the production of small, soluble muropeptides. One milliliter of 11.5 mg/ml purified peptidoglycan was harvested by centrifugation (13,000 g, 5 min, 4° C.) and resuspended in 1 ml conjugation buffer, supplied with the Imject SuperCarrier EDC System for Peptides (Pierce, cat. no. 77152). Twenty-five microliters Cellosyl (2 mg/ml; Hoechst) was added to the PepG suspension and incubated at 37° C. with rotary mixing for 7 hours. The sample was then boiled for 10 min and any insoluble material removed by centrifugation as above. Three hundred microliters of cellosyl-digested PepG was added to 200 µl of conjugation buffer.

Preparation of SuperCarrier (Pierce, cat. no. 77152), conjugation and purification of conjugate were performed as per manufacturers protocol. The PepG conjugate was stored at −20° C.

Immunization of Mice

To produce monoclonal antibodies directed against *B. subtilis* PepG, immunizations were carried out using four 8–12 week old BALB/C mice, obtained from Sheffield University Field Laboratories. The immunogen for the primary immunization was *B. subtilis* PepG, prepared as muropeptide conjugate (described above). For each mouse, 50 µg of conjugate in 50 µL of PBS was mixed with 50 µl of Freund's complete adjuvant, and this mixture was injected subcutaneously.

At about day 14, 29, 113, and 232 following the primary immunization, each mouse was injected intraperitoneally with 50 µg of conjugate in 50 µL of PBS, which had been mixed with 50 µl of Freund's incomplete adjuvant. Hybridomas were generated four days after the final boost of PepG conjugate.

Generation of Hybridomas

Hybridomas were prepared by the general methods of Shulman, Wilde and Kohler and Bartal and Hirshaut (2, 28). Spleen cells from immunized mice 1 and 2 were pooled and were mixed with SP2/0 mouse myeloma cells at a ratio of 5 spleen cells per SP2/0 cell, pelleted by centrifugation (770× g, 5 minutes at 30° C.) and washed in serum-free RPMI. One milliliter of PEG 1500 (50% in 75 mM HEPES, Boehringer cat. no. 783 641) was added over 1 minute, followed by 1 ml of RPMI over 1 minute, and then 9 ml of RPMI over 2 minutes. Cells were then pelleted by centrifugation at 430×g for 15 minutes at 30° C. Cells were resuspended in RPMI-1640/HAT (1 ml of 50× HAT concentrate (Invitrogen cat no. 21060-017) in 50 ml RPMI-1640) containing 20% FCS at approximately 1×10$^6$ cells/ml. One hundred microliters of cell suspension was added to each well of ten 96-well plates and grown at 37° C. Unfused SP2/0 cells were used as a selection control and died 5 days after plating.

Thirteen days after preparation of the hybridomas, supernatants from all wells were assayed by ELISA for the presence of antibodies that bind PepG. Thirteen of 829 wells tested were positive.

Based on the results of the ELISA, positive cells were expanded in a 24-well culture plate and retested for stable antibody secretion by ELISA. Six lines were found to secrete antibodies to PepG. Line BB4 was found to produce antibodies with the highest affinity to *B. subtilis* cell walls. At about 75% confluence, BB4 was cloned by limiting dilution and the subclones retested for anti-PepG antibody secretion. Two clones, BB4/A4 and BB4/A5, were found to secrete antibodies to *B. subtilis* PepG. Isotype determination, using Isotype Strips (Roche Diagnostics, cat. no. 1493027), showed that both antibodies were IgG.

Example 3

Substrate Affinities of PepG Antibodies

Cellosyl Digestion of PepG

PepG from *Bacillus subtilis*, *Staphylococcus aureus*, *Streptococcus mutans*, *Bacillus megaterium*, *Enterococcus faecalis*, *Staphylococcus epidermidis*, and *Listeria monocytogenes* was purified as described in Example 2. One milliliter of each PepG (10 mg/ml) in 25 mM sodium phosphate buffer pH5.6 was digested with 250 µg/ml cellosyl (Hoechst AG) for 15 hours at 37° C. The samples were boiled for 3 minutes to stop the reaction and insoluble material was removed by centrifugation (14,000×g for 8 minutes at room temperature). The soluble cellosyl-digested PepG was stored at −20C.

Staphylococcal PepG has a unique pentaglycine crossbridge, which can be cleaved by lysostaphin, a glycine-gycine endopeptidase. Lysostaphin (25 µg/ml; Sigma Cat No. L0761) was added to the cellosyl digestion of *S. aureus* and *S. epidermidis* PepG to cleave this peptide cross bridge. *S. aureus* was also digested without lysostaphin.

ELISA to Determine Antibody Affinities for PepG and Cellosyl-digested PepG

Three hybridoma lines, identified as 11-232.3, 11-248.2, and 11-569.3 (QED Biosciences), were produced by immunizing mice with UV-inactivated whole *S. aureus*, and the MAbs they produce were subsequently shown to bind to PepG. The affinities of the MAbs produced by 11-232.3 (when purified, the MAb is referred to as 702PG), 11-248.2, and 11-569.3, BB4/A4, and BB4/A5 for PepG from various bacteria, and cellosyl-digested PepG from various bacteria, were compared by ELISA as follows. 96-well immunoassay plates (NUNC Immunoplate Maxisorp) were coated with 100 µg/ml poly-L-lysine (Sigma Chemicals, cat. no. P6407) in 0.05 M carbonate/bicarbonate buffer pH 9.6 (0.015 M $Na_2CO_3$, 0.035 M $NaHCO_3$, pH 9.6, hereafter referred to as carbonate buffer) for 1 hour at room temperature. The carbonate buffer was removed, and the wells were washed once with carbonate buffer. The wells were then coated with 100 µl 5 µg/ml purified PepG substrate, or cellosyl-digested PepG substrate, in carbonate buffer overnight at 4° C. The substrate solution was removed, and the wells were washed twice with PBS-T. The wells were then blocked with 150 µl PBS-T containing 0.2% w/v bovine gelatin (Sigma cat. no. A7030; blocking buffer) for 2 hours at 37° C. The blocking buffer was removed and the wells were washed four times with PBS-T.

Fifty microliters of one of the MAbs listed above (diluted appropriately in blocking buffer) was added to each well and the binding reaction was incubated for 2 hours at 37° C. The monoclonal antibody was removed and the wells were washed three times in PBS-T. Fifty microliters of HRP-conjugated goat anti-mouse IgG (Biorad), diluted 1:20,000 in blocking buffer, was added to each well and the binding reaction was incubated for 1 hour at 37° C. The secondary antibody was removed and the wells were washed three times with PBS-T. Fifty microliters of TMB enzyme substrate (Biorad cat. no. 172-1068) was added to each well and the color was developed for fifteen minutes at room temperature. The reaction was stopped by addition of 50 µl of 2M $H_2SO_4$ to each well, and the absorbance was read on a VICTOR plate reader (Wallac) at 450 nm. The results of the ELISA are shown in Table 6.

Table 6 demonstrates that the PepG antibodies described are not identical, as each shows a different range of specificity and affinity for the different PepG substrates. Specifically, 702PG, MAb-11-232.3, and MAb-11-248.2 show high affinity for *S. aureus* PepG, and low affinity for *B. subtilis* PepG, while the antibodies produced by BB4/A4 and BB4/A5 (also called MAb-BB4/A4 and MAb-BB4/A5) show the reverse specificity. MAb-BB4/A4 and MAb-BB4/A5 also show high affinity for *S. epidermidis*, while the others do not.

MAb-11-569.3, on the other hand, is unaffected by cellosyl digestion, indicating that it may interact with an epitope that is not associated with the bond that is cleaved. The cellosyl/lysostaphin results further confirm the single digest results.

Finally, *S. aureus* PepG has a higher level of O-acetylation on glucosamine residues than PepG from *B. subtilis*, suggesting that this O-acetylation may be important for the binding of antibodies 702PG, MAb-11-232.3, and MAb-11-248.2, and may negatively affect the binding of MAb-BB4/A4 and MAb-BB4/A5.

Example 4

Binding of the Monoclonal Antibodies to LTA, PepG and *Staphylococci*

MAb-11-232.3, MAb-11-248.2, MAb-11-569.3, and MAb-99-110FC12 IE4 were assayed for binding to *S. aureus*

TABLE 6

Binding of PepG antibodies to bacterial substrates

| | Conc. of MAB (µg/ml) that gave reading >0.1 at 450 nm. | | | | | |
|---|---|---|---|---|---|---|
| PepG from: | 702 PG * | 11-232.3 | 11-248.2 | 11-569.3 | BB4/A4 | BB4/A5 |
| *Bacillus subtilis* 168 HR | 1000 | 1000 | >1000 | 100 | <1 | <1 |
| *Staphylococcus aureus* 8325/4 | <1 | <1 | <1 | 100 | 100 | 100 |
| *Streptococcus mutans* LTII | >1000 | 1000 | >1000 | 100 | 100 | 100 |
| *Bacillus megaterium* KM spore cortex | >1000 | >1000 | >1000 | 1000 | 1000 | 1000 |
| *Enterococcus faecalis* NCTC 775 | >1000 | >1000 | >1000 | 100 | 100 | 1000 |
| *Staphylococcus epidermidis* 138 | 100 | 100 | 100 | 100 | <1 | <1 |
| *Listeria monocytogenes* EGD | >1000 | >1000 | >1000 | 1000 | 1000 | 1000 |
| *Bacillus subtilis* 168 HR Cellosyl digested | >1000 | 1000 | >1000 | 100 | 100 | 100 |
| *Staphylococcus aureus* 8325/4 Cellosyl digested | >1000 | 1000 | 100 | 100 | 100 | 100 |
| *Streptococcus mutans* LTII Cellosyl digested | >1000 | 1000 | >1000 | 100 | 100 | 10 |
| *Bacillus megaterium* KM spore cortex Cellosyl digested | >1000 | >1000 | >1000 | 100 | 100 | 1000 |
| *Enterococcus faecalis* NCTC 775 Cellosyl digested | >1000 | >1000 | >1000 | 100 | 100 | 100 |
| *Staphylococcus epidermidis* 138 Cellosyl and lysostaphin digested | 100 | >1000 | 100 | 1000 | 100 | 100 |
| *Listeria monocytogenes* EGD Cellosyl digested | >1000 | >1000 | >1000 | 100 | 100 | 1000 |
| *Staphylococcus aureus* 8325/4 Cellosyl and lysostaphin digested | 100 | >1000 | >1000 | 1000 | 1000 | 1000 |

*Bacillus subtilis* 168 HR was a gift from Howard Roger, University of Kent, U.K.
*Staphylococcus aureus* 8325/4 was a gift from Richard Novick, Skirball Institute, NY, U.S.A.
*Streptococcus mutans* LTII was a gift from Roy Russell, University of Newcastle, U.K.
*Bacillus megaterium* KM was a gift from Keith Johnstone, University of Cambridge, U.K.
*Staphylococcus epidermidis* 138 was a gift from Paul Williams, University of Nottingham, U.K.
*Listeria monocytogenes* EGD was a gift from W. Goebel, University of Wurzburg, Germany Cellosyl digestion, which cleaves glycan strands, of any of the PepG substrates abrogates binding of antibodies 702PG, MAb-11-232.3, MAb-11-248.2, MAb-BB4/A4, and MAb-BB4/A5. Thus, these antibodies may interact with an epitope that requires an intact glycan strand. The affinity of PepG, *S. aureus* LTA, and to methanol-fixed *S. aureus* and methanol-fixed *S. epidermidis*. In addition to those MAbs, a human/mouse chimeric anti-LTA antibody, referred to as A110, was included in the assays as a positive control for LTA and *S. epidermidis* binding. A description of the production and chimerization of A110 can be found in U.S. patent application Ser. No. 09/097,055, filed Jun. 15, 1998.

As shown in Table 7, MAb-11-232.3, 11-248.2 ascites, and 99-110FC12 IE4 supernatant all bound strongly to *S. aureus* PepG. As expected, A110, the anti-LTA antibody, does not bind to PepG.

with PepG. As expected, MAb-99-110FC12 IE4, which was raised to purified *S. aureus* PepG, binds to PepG, but not LTA, quite strongly.

Each of the MAbs was also tested on plates coated with methanol-fixed *S. epidermidis* strain Hay and *S. aureus*, as shown in Tables 9 and 10, respectively.

TABLE 7

Binding of MAbs on Wells Coated with *S. aureus* Peptidoglycan

| Purified Antibody (µg/ml) | 11-232.3 Purified Ms IgG$_3$ | 11-569.3 Purified Ms IgG$_3$ | *A110 Purified Hu IgG$_1$ | Ascites Dilution | 11-248.2 Ascites Ms IgM | Supernatant Dilution | 99-110FC12 IE4 sup. Ms IgM |
|---|---|---|---|---|---|---|---|
| 3 | 3.674 | 0.449 | 0.086 | 100 | 3.903 | 10 | 3.789 |
| 1 | 3.642 | 0.311 | 0.077 | 300 | 4.000 | 30 | 3.983 |
| 0.33 | 3.659 | 0.160 | 0.069 | 900 | 4.000 | 90 | 3.974 |
| 0.11 | 3.085 | 0.104 | 0.066 | 2700 | 4.000 | 270 | 4.000 |
| 0.037 | 2.113 | 0.086 | 0.068 | 8100 | 3.902 | 810 | 3.858 |
| None | 0.074 | 0.069 | 0.103 | None | 0.059 | None | 0.070 |

*Negative anti-LTA Control

When tested on LTA, as shown in Table 8, only A110 showed strong binding. No binding was obtained with MAb-11-232.3, MAb-11-569.3, and 99-110FC12 IE4 supernatant. Slight cross-reactivity was obtained with 11-248.2 ascites at a 1:100 dilution, which may be due to high concentrations of non-specific immunoglobulins in the ascites.

All of the antibodies, except MAb-99-110FC12 IE4, bound to *S. epidermidis* strain Hay. Interestingly, MAb-11-569.3 bound to *S. epidermidis* strain Hay more strongly than did MAb-11-232.3, although MAb-11-569.3 bound less strongly to PepG and *S. aureus* than did the MAb-11-232.3. This result indicates that the antigen on the surface of *S. aureus* to which MAb-11-569.3 was raised, which may or

TABLE 8

Binding of MAbs on Wells Coated with *S. aureus* LTA

| Purified Antibody (µg/ml) | 11-232.3 Purified Ms IgG$_3$ | 11-569.3 Purified Ms IgG$_3$ | *A110 Purified Hu IgG$_1$ | Ascites Dilution | 11-248.2 Ascites Ms IgM | Supernatant Dilution | 99-110FC12 IE4 sup. Ms IgM |
|---|---|---|---|---|---|---|---|
| 3 | 0.055 | 0.087 | 3.357 | 100 | 0.404 | 10 | 0.051 |
| 1 | 0.046 | 0.071 | 3.083 | 300 | 0.206 | 30 | 0.052 |
| 0.33 | 0.052 | 0.061 | 1.996 | 900 | 0.131 | 90 | 0.048 |
| 0.11 | 0.043 | 0.049 | 1.077 | 2700 | 0.092 | 270 | 0.047 |
| 0.037 | 0.045 | 0.045 | 0.411 | 8100 | 0.067 | 810 | 0.044 |
| None | 0.048 | 0.045 | 0.081 | None | 0.054 | None | 0.045 |

*Positive control for LTA

These data indicated that MAb-11-232.3 and MAb-11-248.2, which were raised to whole UV-killed *S. aureus*, are specific for PepG on the surface of the bacteria. MAb-11-569.3, which was also raised to UV-killed *S. aureus*, shows much weaker binding to PepG, and no binding to LTA, indicating that it may be specific for PepG, although it may also be specific for another surface antigen, but cross-react may not be PepG, is likely conserved between *S. aureus* and *S. epidermidis*, resulting in strong binding by MAb-11-569.3 to both bacteria. The IgM antibodies (from hybridomas 11-248.2 and 99-110FC12 IE4) were not tested against *S. aureus*, because the immunoassay Protein A method used for the *S. aureus*-coated plates does not work with IgM antibodies, which do not bind to protein.

TABLE 9

Binding of MAbs on Wells Coated with methanol-Fixed *S. epidermidis* Strain Hay

| Purified Antibody (µg/ml) | 11-232.3 Purified Ms IgG$_3$ | 11-569.3 Purified Ms IgG$_3$ | *A110 Purified Hu IgG$_1$ | Ascites Dilution | 11-248.2 Ascites Ms IgM | Supernatant Dilution | 99-110FC12 IE4 sup. Ms IgM |
|---|---|---|---|---|---|---|---|
| 3 | 0.761 | 3.044 | 1.412 | 100 | 2.905 | 10 | 0.078 |
| 1 | 0.518 | 2.672 | 1.324 | 300 | 2.809 | 30 | 0.075 |
| 0.33 | 0.301 | 1.733 | 1.058 | 900 | 2.749 | 90 | 0.073 |

TABLE 9-continued

Binding of MAbs on Wells Coated with
methanol-Fixed *S. epidermidis* Strain Hay

| Purified Antibody (µg/ml) | 11-232.3 Purified Ms IgG$_3$ | 11-569.3 Purified Ms IgG$_3$ | *A110 Purified Hu IgG$_1$ | Ascites Dilution | 11-248.2 Ascites Ms IgM | Supernatant Dilution | 99-110FC12 IE4 sup. Ms IgM |
|---|---|---|---|---|---|---|---|
| 0.11 | 0.150 | 0.476 | 0.664 | 2700 | 2.699 | 270 | 0.069 |
| 0.037 | 0.087 | 0.147 | 0.324 | 8100 | 2.288 | 810 | 0.065 |
| None | 0.054 | 0.052 | 0.089 | None | 0.056 | None | 0.056 |

*Anti-LTA

TABLE 10

Binding of MAbs on Wells Coated with methanol-Fixed *S. aureus* Type 5

| Purified Antibody (µg/ml) | 11-232.3 Purified Ms IgG$_3$ | 11-569.3 Purified Ms IgG$_3$ | *A110 Purified Hu IgG$_1$ | Ascites Dilution | 11-248.2 Ascites Ms IgM | Supernatant Dilution | 99-110FC12 IE4 sup. Ms IgM |
|---|---|---|---|---|---|---|---|
| 3 | 2.687 | 2.233 | 4.000 | ND | ND | ND | ND |
| 1 | 2.371 | 1.083 | 4.000 | ND | ND | ND | ND |
| 0.33 | 1.541 | 0.330 | 4.000 | ND | ND | ND | ND |
| 0.11 | 0.596 | 0.144 | 3.671 | ND | ND | ND | ND |
| 0.037 | 0.201 | 0.087 | 1.095 | ND | ND | ND | ND |
| None | 0.052 | 0.052 | 0.049 | ND | ND | ND | ND |

ND = not determined
*Anti-LTA

As noted above, peptidoglycan is a cell wall component found in Gram-positive bacteria. These assays show MAb-11-232.3, MAb-11-248.2, and MAb-99-110FC12 IE4 bind PepG strongly and do not bind LTA, another cell wall component common to Gram-positive bacteria. MAb-11-569.3 binds PepG less strongly in an ELISA (Table 7) than it binds *S. aureus* type 5 in a methanol-fixed ELISA (Table 10). Differences observed in the binding of the MAbs may be due to the specific epitope bound by the MAbs and the presentation of that epitope in protein and whole-bacteria ELISAs. Alternatively, MAb-11-569.3 may bind to a different antigen, but cross-react with PepG. MAb-11-232.3, 11-248.2 ascites, and MAb-11-569.3 also bind in an ELISA assay to *S. epidermidis* strain Hay. Furthermore, MAb-11-232.3 and MAb-11-569.3 also bind in an ELISA assay to *S. aureus* (binding of 11-248.2 ascites in the ELISA to *S. aureus* could not be determined). The lack of binding of 99-110FC12 IE4 supernatant to *S. epidermidis* strain Hay in the ELISA suggests that this antibody binds an epitope found on *S. aureus* PepG, but not expressed or available for binding in *S. epidermidis* strain Hay.

Example 5

The Opsonophagocytic Activity of the Monoclonal Antibodies

Antibodies that bind to an antigen may not necessarily enhance opsonization or enhance protection from infection. Therefore, a neutrophil mediated bactericidal assay was used to determine the functional activity of anti-PepG MAb against *S. aureus* and *S. epidermidis* strain Hay. Neutrophils (PMNs) were isolated from adult venous blood by using PMN separation medium (Robbins Scientific Cat. No. 1068-00-0). Forty microliters of PMNs were added to round-bottomed wells of micro titer plates (approximately 2×10$^6$ cells per well) with approximately 3×10$^4$ mid-log phase bacteria. Human serum, treated with Protein G and Protein L to remove antibodies that bind to *S. aureus* and *S. epidermidis* strain Hay, was used as a source of active complement. Forty microliters of antibody was added to the wells at various dilutions and the plates were incubated at 37° C. with constant, vigorous shaking. Samples of 10 µl were taken from each well at zero time and after 2 hours of incubation. Each was diluted, vigorously vortexed to disperse the bacteria, and cultured on blood agar plates overnight at 37° C. to quantitate the number of viable bacteria.

Results are presented as percent reduction in numbers of bacterial colonies observed compared to control samples. In an opsonophagocytic bactericidal assay, 99-110FC12 IE4 supernatant was active against *S. aureus* type 5, but not against *S. epidermidis* strain Hay as shown in Table 11.

TABLE 11

Opsonophagocytic Activity of 99-110FC12 IE4 supernatant
Percent Killed

| Antibody Dilution | *S. aur.* type 5 | *S. epi.* Hay |
|---|---|---|
| neat + PMN + C | 84 | 0 |
| 1:2 + PMN + C | 80 | N.D. |
| 1:4 + PMN + C | 68 | 0 |
| PMN + C | 30 | 9 |
| MAb alone | 0 | 0 |

N.D. = not determined

Hybridoma 99-110FC12 IE4 was produced by immunization of mice with PepG, while hybridomas 11-232.3, 11-248.2, and 11-569.3, were produced by immunizing mice with UV-inactivated whole *S. aureus*. Each of the anti-PepG MAbs from the hybridoma lines was tested for activity in the opsonophagocytic bactericidal assay. In addition, A110, which binds LTA, was also included in the assay. The MAbs produced by 11-232.3 and 11-569.3 are mouse IgG$_3$, kappa light chain antibodies, and were purified before use. A110, which is a human/mouse chimeric antibody with a human IgG$_1$ and a kappa light chain, was also purified before use. MAb-99-110FC12 IE4 and MAb-11-248.2 are mouse IgM, kappa light chain antibodies and were used as either cell culture supernatant (99-110FC12 IE4) or as ascites (11-248.2). Opsonic studies were performed to determine if the MAbs enhanced phagocytosis and killing of both groups of staphylococci.

As shown in Table 12A, each of the anti-PepG antibodies demonstrated enhanced killing of S. aureus. When PMNs were mixed with complement but without antibody, killing of the S. aureus was less than 20%. However, addition of MAb-11-232.3 or MAb-11-569.3 at 100 µg/ml resulted in killing of 76% and 82%, respectively. The use of undiluted ascites from 11-248.2 (a mouse IgM) resulted in killing of 89%, while 75% killing was obtained with neat supernatant from 99-110FC12 IE4 (also a mouse IgM). Surprisingly, although A110 binds strongly to S. aureus LTA (Table 8), and to methanol-fixed S. aureus (Table 10), it shows very weak opsonization of S. aureus in this assay.

TABLE 12A

Opsonophagocytic Killing of S. aureus Type 5 By Monoclonal Antibodies

| Antibody or Hybridoma ID | Isotype | Target Antigen | Conc. (µg/ml) or Dilution | % Killed S. aureus |
|---|---|---|---|---|
| A110 | Human IgG$_1$, kappa | LTA | 300<br>100<br>33.3 | 9<br>23<br>20 |
| MAb-11-232.3 | Mouse IgG$_3$, kappa | Peptidoglycan | 100<br>33.3 | 76<br>63 |
| MAb-11-569.3 | Mouse IgG$_3$, kappa | Peptidoglycan | 100<br>33.3 | 82<br>53 |
| 11-248.2 ascites | Mouse IgM, kappa | Peptidoglycan | Neat<br>1:4<br>1:16 | 89<br>49<br>49 |
| 99-110FC12IE4 supernatant | Mouse IgM, kappa | Peptidoglycan | Neat<br>1:2 | 75<br>51 |

Background killing (PMNs and complement without antibody) was less than 20% for all assays Previous assays have demonstrated stronger opsonization of S. aureus by M110, the mouse monoclonal antibody from which A110 is derived (Table 12B and U.S. patent application Ser. No. 09/097,055). We believe that the difference in activity between A110 and M110 is due to dosage effects in the assays, rather than activity differences between the chimeric and nonchimeric antibodies. As demonstrated in Table 13, A110 retains its activity against S. epidermidis.

TABLE 12B

Opsonophagocytic Killing of S. aureus Type 5 by M110

| Group Description | Ab Dilution | % Killed S. epidermidis | % Killed S. aureus |
|---|---|---|---|
| C' only | | 0.0 | 0.0 |
| PMN only | | 0.0 | 0.0 |
| PMN + C' No Ab | | 49.5 | 53.7 |
| PMN + Ab + C' | 10 | — | 83.3 |
| | 40 | — | 78.9 |
| | 80 | 100.0 | 61.0 |

When S. epidermidis strain Hay was used as the target organism, the results for MAb-11-232.3, 11-248.2 ascites, and MAb-11-569.3 were similar to those obtained with S. aureus type 5, as shown in Table 13. At 300 µg/ml, 66% and 83% killing was obtained with MAb-11-232.3 and MAb-11-569.3, respectively. 95% killing was obtained with neat ascites from hybridoma 11-248.2. However, no killing was obtained with supernatant from 99-110FC12 IE4, which is consistent with its very poor binding to methanol-fixed S. epidermidis in Table 9. Finally, strong killing (>98%) was obtained with A110 at all doses tested (11.1 µg/ml-300 µg/ml), and background killing, obtained by mixing PMNs with complement, but without antibody, was 22%.

TABLE 13

Opsonophagocytic Killing of S. epidermidis Strain Hay By Monoclonal Antibodies

| Antibody or Hybridoma ID | Isotype | Target Antigen | Conc. (µg/ml) or Dilution | % Killed Strain Hay |
|---|---|---|---|---|
| A110 | Human IgG$_1$, kappa | LTA (S. epi. strain Hay) | 300<br>100<br>33.3<br>11.1 | 100<br>99<br>98<br>100 |
| MAb-11-232.3 | Mouse IgG$_3$, kappa | Peptidoglycan | 300<br>100<br>33.3<br>11.1 | 66<br>41<br>41<br>51 |
| MAb-11-569.3 | Mouse IgG$_3$, kappa | Peptidoglycan | 300<br>100<br>33.3<br>11.1 | 83<br>74<br>61<br>59 |
| 11-248.2 ascites | Mouse IgM, kappa | Peptidoglycan | neat<br>1:2<br>1:4 | 95<br>31<br>24 |
| 99-110FC12IE4 supernatant | Mouse IgM, kappa | Peptidoglycan | neat<br>1:4 | 0<br>1 |

Background killing (PMNs and complement without antibody) was less than 22% for all assays.

These data show that the MAb-11-232.3, 11-248.2 ascites, and MAb-11-569.3 can enhance phagocytosis and killing of S. aureus type 5 and S. epidermidis strain Hay. The data also show that A110 is less effective against S. aureus than MAb-11-232.3, 11-248.2 ascites, and MAb-11-569.3, but is highly active against S. epidermidis strain Hay. The 99-110FC12 IE4 supernatant is active against S. aureus, but not S. epidermidis strain Hay. These data demonstrate a strong correlation between binding to methanol-fixed bacteria and the ability to enhance opsonization of those bacteria, with the notable exception of A110, which, although it binds strongly to methanol-fixed S. aureus, is only weakly opsonic against live S. aureus.

Example 6

Nasal Colonization Assay

Using a staphylococcal nasal colonization model in mice, we demonstrated that intranasal instillation of the MAb-11-232.3 significantly reduces nasal colonization.

To ensure that the blocking of nasal colonization obtained with the test MAbs was specific for anti-staphylococcal antibodies, we examined the capacity of an irrelevant control chimeric IgG to block staphylococcal nasal colonization. The control was Medi 493, a chimeric IgG$_1$ MAb against RSV (MedImmune, Inc.). In the same experiment, we also tested MAb-11-232.3 for its capacity to block colonization.

Streptomycin resistant S. aureus type 5 (SA5, 1 to 3×10$^8$ bacteria/mouse) was preincubated for 1 hour in saline (0.9%

NaCl in water), saline containing MAb-11-232.3 (2–3 mg purified IgG per mouse dose of $1-3\times10^8$ bacteria) or saline containing Medi 493 (2–3 mg purified IgG/mouse dose of $1-3\times10^8$ bacteria). Following preincubation, the bacteria were pelleted and resuspended in saline (10 µl/mouse dose),, in saline containing MAb-11-232.3 (10 µl/mouse dose), or in saline containing Medi 493 (10 µl/mouse dose). Eight or nine mice each were intranasally instilled with SA5 in saline, SA5 in MAb-11-232.3, or SA5 in Medi 493. After seven days, the mice were sacrificed and the nasal tissue dissected and plated on Columbia blood agar and tryptic soy agar containing streptomycin to determine colonization. Table 14 shows that MAb-11-232.3 reduced staphylococcal nasal colonization in mice, but that an anti-RSV MAb, Medi 493, had no effect.

TABLE 14

Nasal Colonization Assay against *S. aureus* Type 5

| $2 \times 10^8$ SA5 instilled with: | Number of mice colonized | Average number of colonies recovered |
|---|---|---|
| Sterile Saline | 9/9 | 70 |
| MAb-11-232.3 (2 mg/mouse dose) | 3/8 | 8 |
| Medi 493 (2 mg/mouse dose) | 9/9 | 137 |

Specifically, Table 14 shows that both the number of mice colonized, and the number of colonies, are reduced in an antibody-specific manner by anti-*S. aureus* surface antigen-specific MAb-11-232.3. All of the mice in the saline and the irrelevant chimeric IgG control groups were colonized with *S. aureus*, but only three out of eight mice were colonized in the MAb-11-232.3 group. This reduction in the number of mice colonized demonstrates that the administered MAb 11-232.3 is protective because five of the—eight mice are free from bacterial colonization. The number of colonies recovered per mouse in the MAb-11-232.3 group was also dramatically reduced as compared with the other two groups. The saline control group exhibited an average of 70 colonies in the nine mice colonized and the irrelevant antibody control group exhibited even greater number of average colonies, 187, in the nine mice colonized. In contrast, only three of the eight animals in the treated group exhibited any sign of colonization and that level of colonization, an average of 8 colonies per mouse nose, was greatly reduced. Such a reduction in colonies recovered is similarly profylactically beneficial in vivo. Therefore, the administered anti-PepG MAb is protective from *S. aureus* nasal colonization. These data also demonstrate that the effect is specific for anti-staphylococcal surface antigen MAbs, and is not just a general consequence of antibody binding through the Fc portion of the antibody to surface Protein A on the *staphylococci*. Additional MAbs against *S. aureus* peptidoglycan, MAb-11-248.2 and MAb-11-569.3, may demonstrate similar inhibitory effects on *S. aureus* colonization as described above. Studies are in progress to affirm the effectiveness of MAb-11-248.2 and MAb-11-569.3 in the in vivo mouse model described above.

Example 7

Subcloning of Hybridoma 11-232.3 to Produce Hybridoma 11-232.3 IE9

QED cell culture 11-232.3 was cloned by limiting dilution. Briefly, the cells were diluted to a concentration of 225 viable cells per ml. One ml of this suspension was added to 36 ml of RPMI 1640. The cell suspension was further diluted by the addition of 7.5 ml of FBS, 0.5 ml of 10 mg/ml kanamycin solution (Gibco BRL Cat #15160-054) and 5 ml of Hybridoma SFM medium (Gibco BRL Cat #12045-084). The final volume of the suspension was 50 ml, resulting in a cell concentration of 4.5 cells/ml. Two hundred microliters of the cell suspension was added to each well of two 96-well tissue culture dishes. The cultures were incubated for 10 days at 37° C. in a humidified atmosphere of 5% $CO_2$ in air. The presence of clones was verified by microscopic observation of single foci of cells in individual wells. Approximately 40% of all wells had growing clones of 11-232.3. When tested by ELISA, all supernatants bound peptidoglycan. Four cultures, 11-232.3-IG9, -IE9, -IH7 and -IB6 were expanded and cryopreserved. The binding of these four clones to peptidoglycan and LTA is shown in Table 15. The MAb produced by hybridoma 11-232.3 IE9 was subsequently designated M130.

TABLE 15

Binding of 11-232.3 subclones to LTA and PepG

| Culture ID | Supernatant Dilution | Absorbance of PepG | Absorbance on LTA |
|---|---|---|---|
| 232.3 uncloned | 2 | 4.000 | 0.090 |
| 232.3 uncloned | 2 | 4.000 | 0.084 |
| 232.3IG9 | 2 | 3.384 | 0.084 |
| 232.3IE9 | 2 | 3.141 | 0.100 |
| 232.3IH7 | 2 | 2.863 | 0.092 |
| 232.3IB6 | 2 | 3.570 | 0.086 |
| Buffer Only | | 0.090 | 0.075 |

As shown in Table 16, the monoclonal antibody produced by hybridoma 11-232.3 IE9, M130, bound *S. aureus* in the LBE assay. Surprisingly, M130 did not bind to *S. epidermidis* strain Hay in this assay, although it shows opsonic activity against *S. epidermidis* strain Hay (Table 7). The opsonic assay uses antibody at a concentration of up to 300 µg/ml, while the LBE assay uses concentrations of up to 3 µg/ml, so the difference in the activity of M130 in the two assays may result from the large difference in concentrations used.

TABLE 16

Binding of MAb M130 by LBE Assay

| Antibody µg/ml | SA5 USU | SA5 ATCC 49521 | SA8 ATCC 12605 | S. hemo ATCC 43252 | S. epi Hay |
|---|---|---|---|---|---|
| 3 | 2.981 | 2.319 | 2.365 | 0.133 | 0.101 |
| 1 | 1.765 | 1.457 | 1.313 | 0.120 | 0.082 |
| 0.33 | 0.633 | 0.641 | 0.441 | 0.120 | 0.072 |
| 0.11 | 0.252 | 0.248 | 0.155 | 0.112 | 0.076 |
| Buffer | 0.100 | 0.808 | 0.110 | 0.120 | 0.072 |

Example 8

Cloning and Sequencing of the M130 Variable Regions

Total RNA was isolated from $2\times10^6$ frozen IE9 (232-3) hybridoma cells using the Midi RNA Isolation kit (Qiagen) following the manufacturer's procedure. The RNA was dissolved in 10 mM Tris, 0.1 mM EDTA (pH 8.4) containing of 0.25 µg/µl Prime RNase Inhibitor (0.03 U/µg; Sigma).

FIG. 1 shows the strategy for cloning the variable region genes. Table 17 shows the sequences of the oligonucleotide primers used for the procedures (SEQ ID NOS: 5–12). The total RNA (2 µg) was converted to cDNA by using Superscript II-MMLV Reverse Transcriptase (Life Technologies) and mouse Kappa-specific primer (JSBX-18; SEQ ID NO: 8; Sigma-Genosys) and a mouse heavy chain-specific primer (JSBX-25A; SEQ ID NO: 9; Sigma-Genosys) according to the manufacturer's procedures (see Table 12 for primer sequences). The first strand cDNA synthesis products were purified using a Centricon-30 concentrator device (Amicon). Of the 40 µl of cDNA recovered, 5 µl was used as template DNA for PCR. PCR amplification reactions (50 µl) contained template DNA, 30 pmoles of the appropriate primers (JSBX-11A, -12A and -18 for light chains; SEQ ID NOS: 6–8; JSBX-5 and -25A for heavy chains; SEQ ID NO: 5 and SEQ ID NO: 9), 2.5 units of ExTaq polymerase (PanVera), 1×ExTaq reaction buffer, 200 µM each dNTP, 2 mM MgCl$_2$. The template was denatured by an initial incubation at 96° C. for 3 min. The products were amplified by 30 thermal cycles of 96° C. for 1 min., 60° C. for 30 sec., 72° C. for 30 sec. The PCR products from the successful reactions were purified using the Nucleospin PCR Purification system (Clontech) as per manufacturer's procedure.

consensus DNA sequence of the light and heavy chain variable regions is shown in FIG. 2 (SEQ ID NO: 2 and SEQ ID NO: 4, respectively).

Example 9

Cloning of Mouse/Human Chimeric Antibody A130

The heavy and light chain variable regions of M130 were then subcloned into a mammalian expression plasmid vector for production of recombinant chimeric mouse/human antibody molecules under the control of CMV transcription promoters. The variable region of M130 is fused directly to the human IgG$_1$ constant domain. The light chain of M130, on the other hand, has a mouse Kappa intron domain 3' of the variable region coding sequence. After splicing, the variable region becomes fused to a human Kappa constant region exon. The selectable marker for both vectors in mammalian cells is Neomycin (G418).

The variable region gene fragments were re-amplified by PCR using primers that adapted the fragments for cloning into the expression vector (FIG. 1, Table 17). The heavy chain front primer (JSBX-44; SEQ ID NO: 11) includes a 5' tail that encodes the C-terminus of the heavy chain leader

TABLE 17

Oligonucleotide primers used

| Name | Length | Description | Oligo Sequence | SEQ ID NO: |
|---|---|---|---|---|
| JSBX-5 | 40 | mouse HCV front primer for MegaVector | TGTTTTCGTACGTCTTGTCCCAGGTBCARCTKMARSARTC | 5 |
| JSBX-11A | 32 | mLCV Front for MegaVector | TACCGTACCGGTGAYATYMAGATGACMCAGWC | 6 |
| JSBX-12A | 32 | mLCV Front for MegaVector | TACCGTACCGGTSAAATTGWKCTSACYCAGTC | 7 |
| JSBX-18 | 23 | Mouse Kappa Constant reverse primer | GCACCTCCAGATGTTAACTGCTC | 8 |
| JSBX-25a | 22 | Mouse IgG reverse primer (123-144) | CTGCACAGGGMTCCAKAGTTCC | 9 |
| JSBX-27 | 38 | Mouse Back Primer for MegaVector | ATAGGATTCGAAAAGTGTACTTMCGTTTCAGYTCCARC | 10 |
| JSBX-44 | 23 | M130 HCV front primer for MegaVector | TGTTTTCGTACGTCTTGTCCCAG | 11 |
| JSBX-45 | 35 | M130 HCV back primer for MegaVector | TTTTCTGAATTCTGCAGAGACAGTGACCAGAGTCC | 12 |

Note: each of the following letters is used to denote an equal mixture of nucleotides in that position: B = C, G, or T; D = A, G, or T; K = G or T; M = A or C; R = A or G; S = C or G; V = A, C, or G; W = A or T; Y = C or T.

The PCR products (approximately 400 base pairs) were then cloned into bacterial vector pGEM T (Promega), a T/A style cloning vector, following the manufacturer's procedures using a 3:1 insert to vector molar ratio. One half (5 µl) of the ligation reactions were used to transform Ultracompetent XL1Blue cells (Stratagene) as per the manufacturer's procedure. Bacterial clones containing plasmids with DNA inserts were identified using diagnostic restriction enzyme digestions with DraIII and BsiWI (for heavy chain clones) or DraIII and EcoRV (for light chain clones) (New England Biolabs). Plasmids containing inserts of the appropriate size (~400 bp) were then sequenced. The pGEM vector containing the M130 heavy chain variable region is referred to as pJSB18-6, and the pGEM vector containing the M130 light chain variable region is referred to as pJSB4-4. The final and a BsiWI restriction site for cloning, while the heavy chain reverse primer (JSBX-45; SEQ ID NO: 12) adds a 3' EcoRI restriction site for cloning. This results in the addition of two amino acids, glutamine (E) and phenylalanine (F) between the heavy chain variable region and the human IgG$_1$ constant region.

The light chain front primer (JSBX-11A; SEQ ID NO: 6) introduces a 5' tail that encodes the two C-terminal amino acids of the light chain leader and an AgeI restriction site for cloning purposes. The light chain reverse primer (JSBX-27; SEQ ID NO: 10) adds a 3' DNA sequence for the joining region-Kappa exon splice junction followed by a BstBI restriction site for cloning. PCRs were performed as described above, using pJSB18-6 as a template for the heavy chain and pJSB4-4 as a template for the light chain. Following a three minute incubation at 96° C. the PCR perimeters were 30 thermal cycles of 58° C. for 30 sec., 70° C. for 30 sec., and 96° C. for 1 min.

Figure 3:
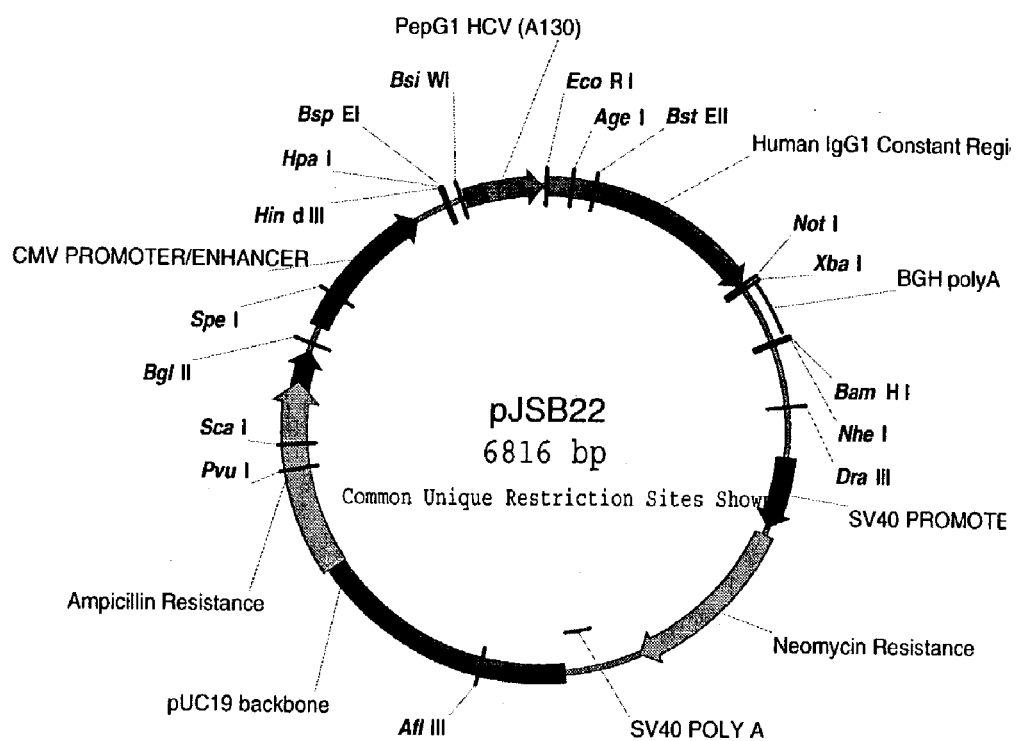
FIG. 3 is shows the pJSB22 heavy chain expression plasmid.

The heavy chain PCR product was digested with BsiWI and EcoRI (New England Biolabs), purified using a Nucleospin PCR Purification column (Clontech), per the manufacturer's instructions, and ligated into BsiWI/EcoRI/PflMI digested and gel-purified pJRS383, using the Takara Ligation Kit (Panvera), per the manufacturer's procedure. The ligation mix was then transformed into XL1Blue cells (Stratagene); clones were selected and screened for the correct insert, resulting in mammalian expression vector pJSB22 (FIG. 3).

Figure 4:
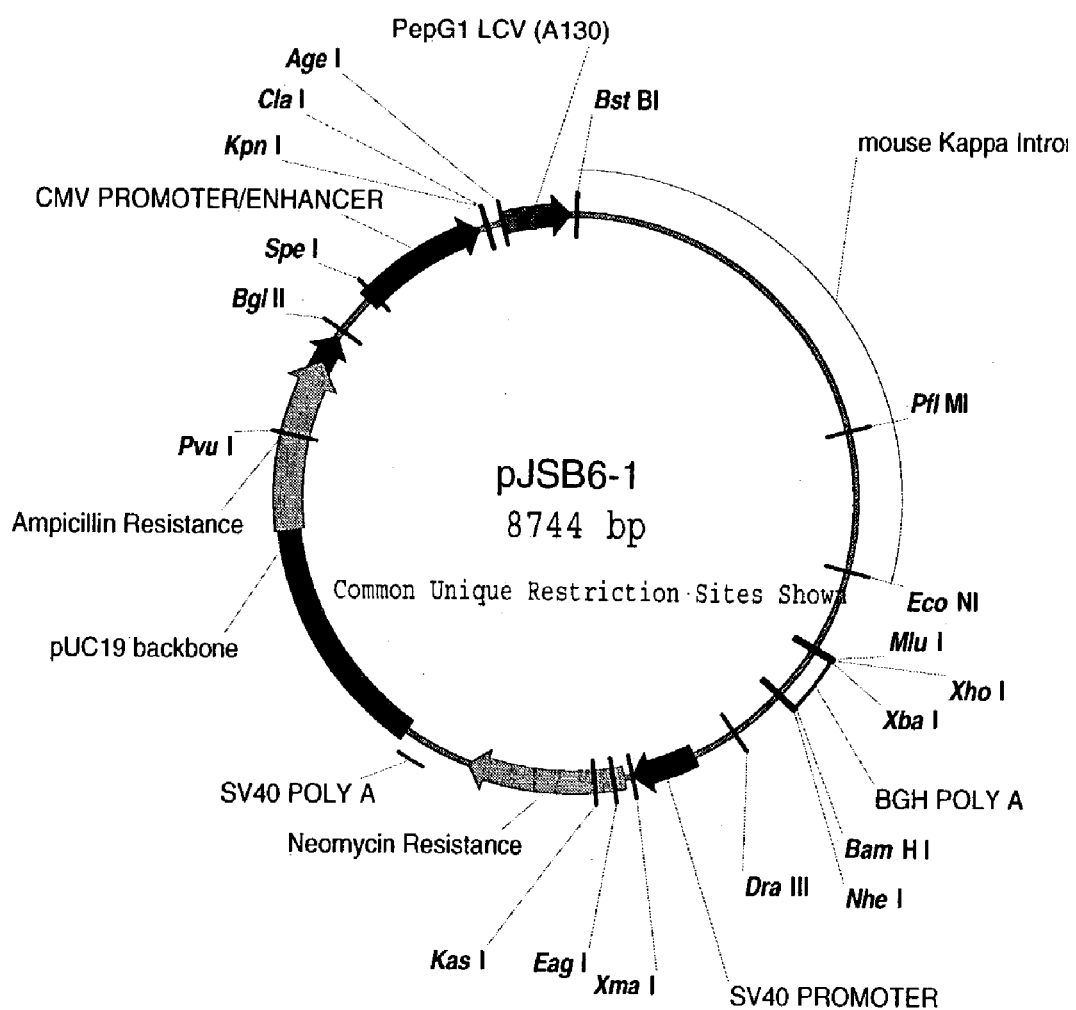
FIG. 4 shows the pJSB6 light chain expression plasmid.

The light chain PCR product (approximately 350 base pairs) was digested with AgeI and BstBI (New England Biolabs), purified using a Nucleospin PCR Purification column (Clontech), as described by the manufacturer. This fragment was then ligated into pJRS384 that had been AgeI/BstBI/XcmI digested and gel-purified, using the Takara Ligation Kit (Panvera), per the manufacturer's procedure. The ligation mix was then transformed into XL1Blue cells (Stratagene); clones were selected and screened for the correct insert, resulting in mammalian expression plasmid pJSB6.1 (see FIG. 4).

Figure 5:
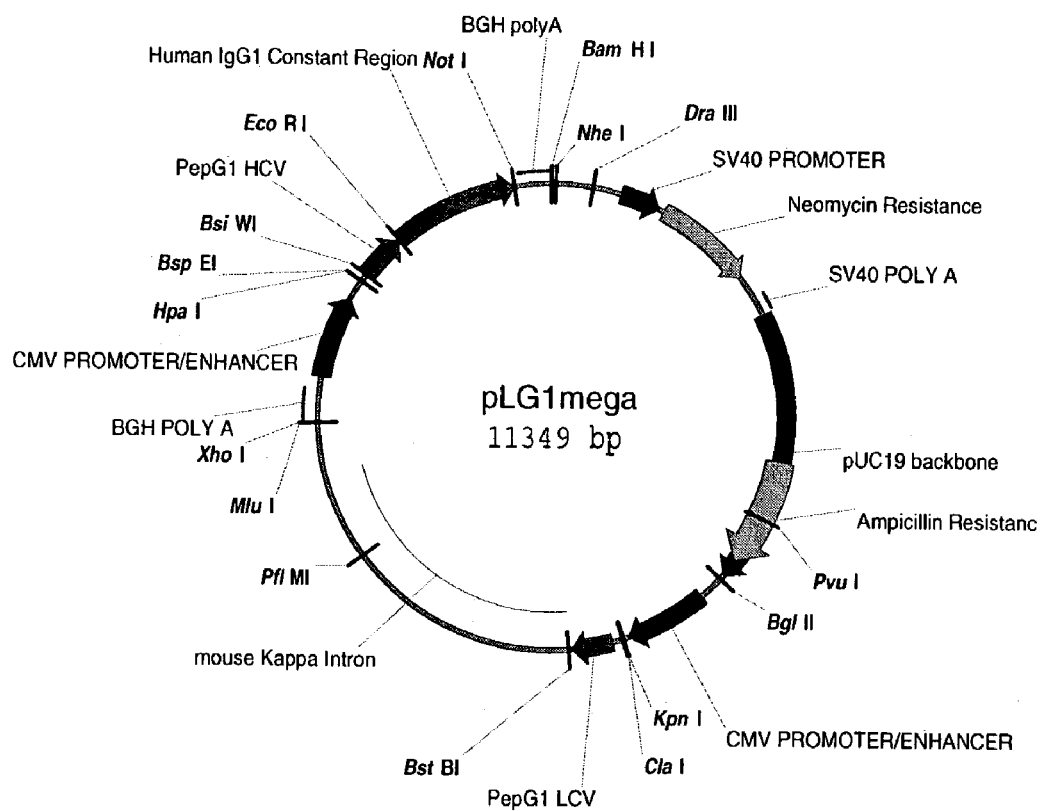
FIG. 5 shows the pLG1 bi-cistronic expression plasmid.

Combining the two individual plasmids then made a single expression construct containing both the light and heavy chain expression cassettes. The plasmid pJSB6.1 was digested with BamHI and NheI (New England Biolabs) and purified using a Nucleospin PCR Purification column (Clontech), as described by the manufacturer. The plasmid pJSB22 was digested with BglII and NheI (New England Biolabs), separated on an agarose gel and the fragment containing the heavy chain expression domain was isolated using a Nucleospin Gel Fragment DNA Purification column (Clontech). These fragments were ligated together using the Takara Ligation Kit (Panvera) following the manufacturer's procedure and transformed into XL1Blue cells (Stratagene). The resulting bi-cistronic expression vector, pLG1-MEGA, was then transfected into mammalian cells for A130 chimeric antibody production, after sequence confirmation of the variable regions (FIG. 5).

Example 10

Transient Production of Recombinant Chimeric Mouse/Human A130 Antibody

The plasmid pLG1-MEGA was transfected into COS-7 (ATCC no. CRL 1651) cells using Superfect (Qiagen) in 6 well tissue culture dishes as described by the manufacturer. After two days the supernatant was assayed for the production of chimeric antibody and for the capability for the expressed antibody to bind to *S. aureus* peptidoglycan antigen as follows.

Figure 6:
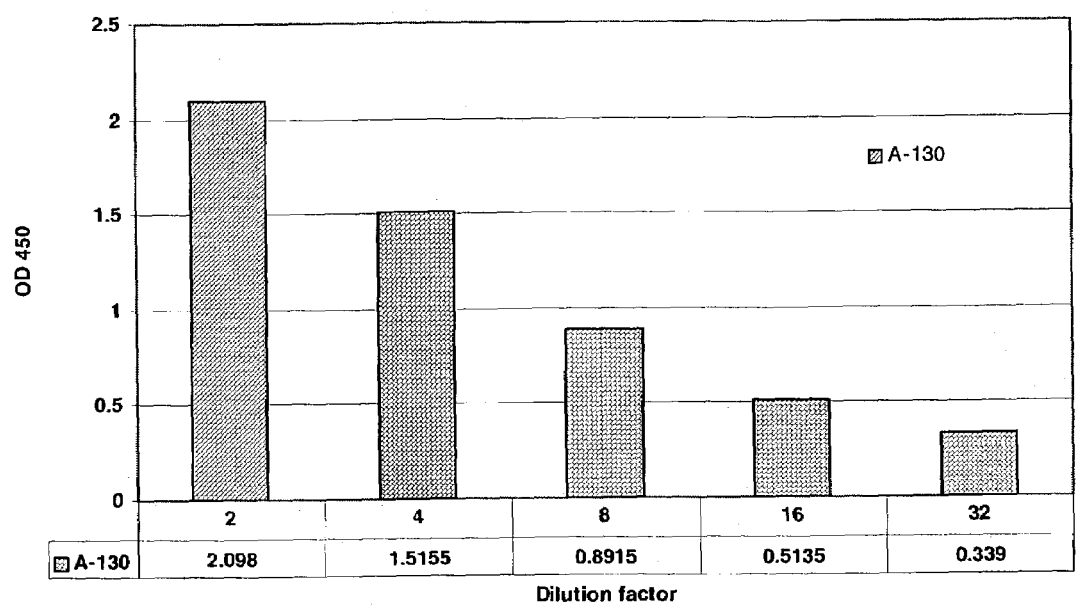
FIG. 6 shows the binding of anti-human IgG to the mouse/human chimeric antibody A130.

8-well strips (Maxisorp F8; Nunc, Inc.) were coated with a 1:500 dilution in PBS of goat anti-human Fc (Pierce). The plates were then covered with pressure sensitive film and incubated overnight at 4° C. Plates were then washed once with 1×Wash solution (KPL cat. no. 50-63-01). One hundred microliters of culture supernatant dilutions were then applied to duplicate wells and allowed to incubate for 60 minutes on a plate rotator at room temperature. The plates were washed seven times with Wash solution. A goat anti-human kappa-HRP (Zymed) conjugate was diluted 1:800 in the sample/conjugate diluent (0.02 M Tris pH 7.4, 0.25 M NaCl$_2$, 2% gelatin, 0.1% Tween-20). One hundred microliters was added to the samples, and then incubated on a plate rotator for 60 minutes at room temperature. The samples were washed seven times, as above and then incubated with 100 µL/well of TMB substrate (BioFx, cat. no. TMBW-0100-01) for <1 minute at room temperature. The reaction was stopped with 100 µL/well of TMB Stop reagent (BioFx, cat. no. STPR-0100-01) and the absorbance value at 450 nm was determined using an automated microtiter plate ELISA reader (Spetramax Plus; Molecular Devices, Inc.). FIG. 6 shows that the mouse/human chimeric A130 antibody is bound by a goat anti-human IgG kappa antibody, indicating that transfection of cells with the pLG1-MEGA plasmid results in the cells producing a molecule containing both human IgG and Kappa domains.

The supernatants were then assayed for the ability of the expressed antibodies to bind to peptidoglycan. 8-well strips (Maxisorp F8; Nunc, Inc.) were coated with a 5 µg/ml solution of *S. aureus* peptidoglycan (prepared by the method set forth in Example 2) in carbonate coating buffer, pH 9.5 (0.1M sodium bicarbonate) overnight at 4° C. Plates were washed once with PBS. One hundred microliters of culture supernatant dilutions were applied to duplicate wells and allowed to incubate for 60 minutes on a plate rotator at room temperature. The plates were washed seven times with Wash solution. One hundred microliters of Goat anti-Human IgG H+L–HRP (Zymed) diluted 1:4000 in sample/conjugate diluent was added to the samples, and the plates were incubated on a plate rotator for 60 minutes at room temperature. The samples were washed seven times with Wash buffer and then incubated with 100 µL/well of TMB substrate (BioFx) for 10–15 minutes on a plate rotator at room temperature. The reaction was stopped with 100 µL/well of TMB Stop reagent (BioFx) and the absorbance value at 450 nm was determined using an automated microtiter plate ELISA reader (Spectramax Plus, Molecular Devices).

Figure 7:
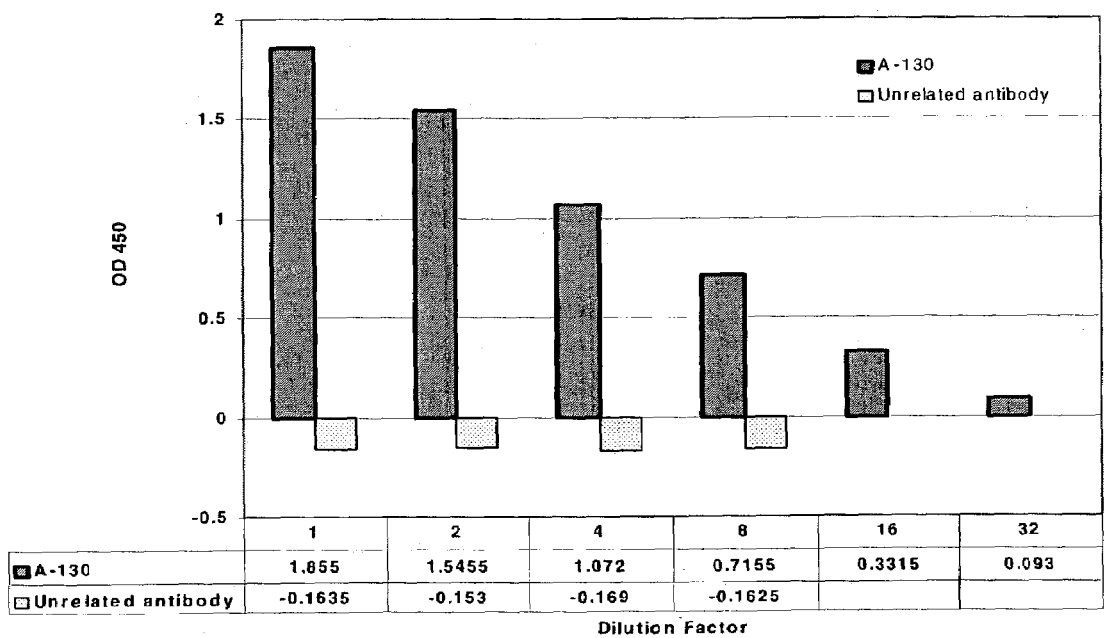
FIG. 7 shows the binding activity of the mouse/human chimeric antibody, A130, to *S. aureus* peptidoglycan.

As a positive control, the original mouse monoclonal antibody M130 was used, and assayed with a 1:2000 dilution of Goat anti-Mouse Fc-HRP conjugate. FIG. 7 shows that the transfection of cells with the pLG1-MEGA plasmid results in the cells producing a molecule that binds to *S. aureus* peptidoglycan. These results suggest that the mouse/human chimeric antibody, A130, retains the peptidoglycan binding ability of the mouse monoclonal antibody M130, from which it was derived.

Example 11

Specific Binding of the Monoclonal Antibodies to PepG

To confirm that the monoclonal antibodies are specific for PepG, and do not bind to a contaminant in the PepG preparation used for the ELISA assay shown in Table 7, sandwich assays were conducted. In brief, multiwell plates were coated with "capture" antibodies specific for PepG, LTA, or an unknown antigen; PepG was then added to the wells and bound by the antibodies; and then a "detection" antibody was added to measure its affinity for the PepG captured by the capture antibody.

Specifically, monoclonal antibodies M110, M 130, MAb-11-230.3, MAb-11-232.3, MAb-11-391.4, MAb-11-557.3, MAb-11-564.4, MAb-11-580.5, and MAb-11-586.3 were diluted to 3 µg/ml in PBS. Hybridomas 11-230.3, 11-232.3, 11-391.4, 11-557.3, 11-564.4, 11-580.5, and 11-586.3 were derived from mice that had been immunized with whole UV-killed *S. aureus*. As set forth above, MAb-11-230.3, MAb-11-232.3, MAb-11-557.3, MAb-11-564.4, and MAb-11-586.3 have been previously shown to bind to PepG, while MAb-11-391.4 binds to LTA, and MAb-11-580.5 binds to an unknown epitope on *S. aureus*. These MAbs were used to coat four columns of Nunc Maxisorp Stripwells (Nunc Cat #469949), and are referred to as "capture" antibodies. Coating of each capture antibody was accomplished by adding 100 µl of the 3 µg/ml solution to the appropriate wells and incubating overnight (18–26 hours) at room temperature. The unbound material was then removed from the wells by washing four times with PBS-T. For each capture antibody, *S. aureus* peptidoglycan (prepared by S. Foster as described in Example 2), diluted to 10 µg/ml in PBS-T, was added to the wells of two of the four columns, and PBS-T without peptidoglycan was added to the wells of the other two columns.

The wells were incubated for 30–60 minutes at room temperature and washed four times with PBS-T. The wells then received 100 µl of A130 at the concentrations indicated in Table 17 (2-fold dilutions from 5 µg/ml to 0.078 µg/ml). An anti-PepG monoclonal antibody, A130, which is described above, was the "detection" antibody and was diluted in PBS-T with 0.1% human serum without IgG, IgA and IgM (Axell Cat BYA20341, Lot H2415). The detection antibody was expected to react with any of the PepG bound to the capture MAbs used for coating. Thus, it was expected that PepG would not be captured in wells coated with MAbs M110 and 391.4, which are specific for LTA, and in wells coated with MAb-11-580.5, a MAb of unknown specificity.

Following another 30–60 minute incubation, the wells were washed with PBS-T and each well received 95 µl of HRP-conjugated gamma-specific goat anti-human IgG (Zymed Cat 62-8420), diluted 1:6000 in PBS-T. After 30–60 minutes, the wells were washed with PBS-T and 100 µl of TMB substrate solution was added to each well (BioFX Cat TMBW-0100-01). The reaction was allowed to proceed for 15 minutes at room temperature in the dark and was stopped by addition of 100 µl TMB Stop Reagent to each well (BioFX Cat STPR-0100-01). The absorbance of each well was measured using a Molecular Devices Vmax microplate reader with a 450 nm filter.

Table 18 shows the results of the capture assay using a battery of capture MAbs, followed by PepG, and then A130 as the detection MAb. After coating a well with MAb-11-230.2, MAb-11-232.3, MAb-11-557.3, MAb-11-564.4, or MAb-11-586.3, and incubating with PepG, the detection antibody, A130, binds to the captured PepG on the plate. If an anti-LTA antibody, such as that produced by hybridoma 391.4, or M110, is used to capture, A130 does not bind, presumably because the capture antibody failed to bind PepG. Furthermore, MAb-11-580.5, which is of unknown specificity, also fails to capture significant PepG, as evidenced by the lack of binding by A130. As a positive control, if M130, which has identical variable regions as A130, is to capture PepG, A130 binds strongly to the plate. These results suggest that A130 binds to PepG, and not to a contaminant in the PepG preparation, because capturing PepG with a battery of a different antibodies that are believed to bind to PepG results in binding of A130 to the captured material.

TABLE 18

PepG Sandwich Assay:
Capture with anti-*S. aureus* MAbs and Detection with A130

| capture MAb → detection MAb ↓ | MAb-11-230.3 (anti-PepG) | | MAb-11-232.3 (anti-PepG) | | MAb-11-391.4 (anti-LTA) | |
|---|---|---|---|---|---|---|
| A130 (µg/ml) | +PepG | −PepG | +PepG | −PepG | +PepG | −PepG |
| 5     | 0.513 | 0.096 | 0.529 | 0.077 | 0.085 | 0.072 |
| 2.5   | 0.576 | 0.090 | 0.529 | 0.073 | 0.088 | 0.069 |
| 1.25  | 0.703 | 0.091 | 0.557 | 0.074 | 0.087 | 0.068 |

TABLE 18-continued

PepG Sandwich Assay:
Capture with anti-*S. aureus* MAbs and Detection with A130

| | | | | | | |
|---|---|---|---|---|---|---|
| 0.625  | 0.561 | 0.091 | 0.526 | 0.072 | 0.085 | 0.074 |
| 0.3125 | 0.493 | 0.093 | 0.450 | 0.072 | 0.084 | 0.072 |
| 0.156  | 0.420 | 0.091 | 0.499 | 0.066 | 0.085 | 0.072 |
| 0.078  | 0.322 | 0.090 | 0.303 | 0.071 | 0.078 | 0.068 |
| Buffer | 0.090 | 0.090 | 0.071 | 0.081 | 0.063 | 0.076 |

| capture MAb → detection MAb ↓ | MAb-11-557.3 (anti-PepG) | | MAb-11-564.4 (anti-PepG) | | MAb-11-580.5 (unknown) | |
|---|---|---|---|---|---|---|
| A130 (µg/ml) | +PepG | −PepG | +PepG | −PepG | +PepG | −PepG |
| 5      | 0.599 | 0.079 | 0.530 | 0.095 | 0.151 | 0.079 |
| 2.5    | 0.610 | 0.076 | 0.564 | 0.093 | 0.159 | 0.082 |
| 1.25   | 0.588 | 0.079 | 0.560 | 0.095 | 0.158 | 0.086 |
| 0.625  | 0.612 | 0.079 | 0.522 | 0.093 | 0.163 | 0.086 |
| 0.3125 | 0.593 | 0.079 | 0.498 | 0.091 | 0.158 | 0.081 |
| 0.156  | 0.525 | 0.078 | 0.432 | 0.091 | 0.151 | 0.085 |
| 0.078  | 0.434 | 0.080 | 0.387 | 0.095 | 0.139 | 0.083 |
| Buffer | 0.081 | 0.078 | 0.093 | 0.090 | 0.080 | 0.088 |

| capture MAb → detection MAb ↓ | MAb-11-586.3 (anti-PepG) | | M110 (anti-LTA) | | M130 (anti-PepG) | |
|---|---|---|---|---|---|---|
| A130 (µg/ml) | +PepG | −PepG | +PepG | −PepG | +PepG | −PepG |
| 5      | 0.635 | 0.088 | 0.182 | 0.172 | 0.723 | 0.072 |
| 2.5    | 0.661 | 0.085 | 0.172 | 0.161 | 0.666 | 0.072 |
| 1.25   | 0.636 | 0.096 | 0.172 | 0.163 | 0.633 | 0.071 |
| 0.625  | 0.524 | 0.085 | 0.169 | 0.156 | 0.568 | 0.070 |
| 0.3125 | 0.599 | 0.085 | 0.169 | 0.153 | 0.467 | 0.083 |
| 0.156  | 0.526 | 0.084 | 0.167 | 0.151 | 0.351 | 0.070 |
| 0.078  | 0.411 | 0.084 | 0.163 | 0.149 | 0.269 | 0.070 |
| Buffer | 0.083 | 0.084 | 0.146 | 0.146 | 0.067 | 0.068 |

To confirm that the anti-PepG antibodies do not bind to possible LTA contamination in the PepG preparation, a similar sandwich assay was conducted in which A110, which binds to LTA, was used as the capture antibody, LTA was bound to the capture antibody, and detection antibodies were then added to measure their binding to the captured LTA.

Nunc Maxisorp Stripwells (Nunc Cat #469949) were coated with 100 µl of 3 µg/ml A110 in PBS and incubated overnight (18–26 hours) at room temperature. After overnight incubation, unbound material was removed from the wells by washing four times with PBS-T. Replicate wells then received 100 µl of LTA solution (Sigma Cat #2515 diluted to 1 µg/ml in PBS-T) or PBS-T alone. The wells were then incubated for 30–60 minutes at room temperature and washed four times with PBS-T.

The wells received 100 µl of an antibody selected from monoclonal antibodies M110, M130, MAb-11-230.3, MAb-11-232.3, MAb-11-391.4, MAb-11-557.3, MAb-11-564.4, MAb-11-580.5, and MAb-11-586.3, titrated in 2-fold dilutions from 5 µg/ml to 0.078 µg/ml in PBS-T with 0.1% human serum without IgG, IgA and IgM (Axell Cat BYA20341, Lot H2415). Each MAb was titrated in four columns, two of which had received LTA and two of which had received PBS-T alone. These mouse MAbs served as detection antibodies, analogous to the A130 detection antibody used in Table 18.

Following another 30–60 minute incubation, the wells were again washed with PBS-T and each well received 95 μl of HRP-conjugated gamma-specific anti-mouse IgG (Jackson Immunoresearch Cat 115-035-164), diluted 1:10,000 in PBS-T. After 30–60 minutes, the wells were washed with PBS-T and 100 μl of TMB substrate solution was added to each well (BioFX Cat TMBW-0100-01). The reaction was allowed to proceed for 15 minutes at room temperature in the dark and stopped by addition of 100 μl TMB Stop Reagent to each well (BioFX Cat STPR-0100-01). The absorbance of each well was, measured using a Molecular Devices Vmax microplate reader with a 450 nm filter.

Table 19 shows the results of the sandwich assay using A110 as the capture antibody, followed by LTA, and then a battery of detection MAbs. This assay confirms that the antibodies that are believed to bind to PepG do not in fact bind to possible LTA contaminants in the PepG preparation. A110 was used as the capture antibody to capture LTA on the plate. MAb-11-230.2, MAb-11-232.3, MAb-11-557.3, MAb-11-564.4, MAb-11-586.3, and M130, all of which bind to PepG, fail to bind to the captured LTA on the plate. As would be expected, the anti-LTA antibodies, including those produced by hybridoma 391.4, and M110, show strong binding to the captured LTA. Finally, MAb-11-580.5, which is of unknown specificity, does not bind to the captured LTA. These results further confirm that the anti-PepG monoclonal antibodies, including M130, do not bind to LTA.

TABLE 19

LTA Sandwich Assay: Capture with A110, Detection with anti-*S. aureus* MAbs

| detection MAb → detection MAb | MAb-11-230.3 (anti-PepG) | | MAb-11-232.3 (anti-PepG) | | MAb-11-391.4 (anti-LTA) | |
|---|---|---|---|---|---|---|
| conc. (μg/ml) | +PepG | −PepG | +PepG | −PepG | +PepG | −PepG |
| 5 | 0.063 | 0.063 | 0.066 | 0.066 | 1.751 | 0.118 |
| 2.5 | 0.059 | 0.080 | 0.073 | 0.065 | 0.930 | 0.090 |
| 1.25 | 0.059 | 0.061 | 0.064 | 0.067 | 0.479 | 0.082 |
| 0.625 | 0.057 | 0.058 | 0.063 | 0.065 | 0.277 | 0.072 |
| 0.3125 | 0.056 | 0.059 | 0.060 | 0.063 | 0.160 | 0.067 |
| 0.156 | 0.059 | 0.061 | 0.061 | 0.066 | 0.113 | 0.066 |
| 0.078 | 0.057 | 0.058 | 0.061 | 0.062 | 0.086 | 0.061 |
| Buffer | 0.055 | 0.058 | 0.066 | 0.064 | 0.060 | 0.063 |

| detection MAb → detection MAb | MAb-11-557.3 (anti-PepG) | | MAb-11-564.4 (anti-PepG) | | MAb-11-580.5 (unknown) | |
|---|---|---|---|---|---|---|
| conc. (μg/ml) | +PepG | −PepG | +PepG | −PepG | +PepG | −PepG |
| 5 | 0.064 | 0.058 | 0.072 | 0.074 | 0.066 | 0.066 |
| 2.5 | 0.056 | 0.056 | 0.065 | 0.067 | 0.064 | 0.063 |
| 1.25 | 0.058 | 0.057 | 0.086 | 0.066 | 0.062 | 0.065 |
| 0.625 | 0.056 | 0.061 | 0.063 | 0.063 | 0.059 | 0.061 |
| 0.3125 | 0.057 | 0.055 | 0.062 | 0.061 | 0.064 | 0.063 |
| 0.156 | 0.058 | 0.059 | 0.060 | 0.062 | 0.059 | 0.062 |
| 0.078 | 0.056 | 0.059 | 0.061 | 0.060 | 0.057 | 0.059 |
| Buffer | 0.054 | 0.056 | 0.084 | 0.061 | 0.054 | 0.059 |

| detection MAb → detection MAb | MAb-11-586.3 (anti-PepG) | | M110 (anti-LTA) | | M130 (anti-PepG) | |
|---|---|---|---|---|---|---|
| conc. (μg/ml) | +PepG | −PepG | +PepG | −PepG | +PepG | −PepG |
| 5 | 0.060 | 0.062 | 0.743 | 0.059 | 0.068 | 0.070 |
| 2.5 | 0.059 | 0.060 | 0.509 | 0.059 | 0.061 | 0.063 |
| 1.25 | 0.061 | 0.062 | 0.362 | 0.062 | 0.060 | 0.063 |
| 0.625 | 0.061 | 0.062 | 0.257 | 0.060 | 0.059 | 0.060 |

TABLE 19-continued

LTA Sandwich Assay: Capture with A110, Detection with anti-*S. aureus* MAbs

| 0.3125 | 0.060 | 0.059 | 0.179 | 0.060 | 0.055 | 0.058 |
|---|---|---|---|---|---|---|
| 0.156 | 0.061 | 0.061 | 0.133 | 0.060 | 0.057 | 0.057 |
| 0.078 | 0.058 | 0.057 | 0.100 | 0.058 | 0.054 | 0.057 |
| Buffer | 0.060 | 0.057 | 0.055 | 0.059 | 0.055 | 0.058 |

Finally, to further confirm that M110 does not capture a contaminant in the PepG preparation that is recognized by M130, the following sandwich assay was performed. M110 was bound to plates as the capture antibody, LTA or PepG was then bound to the plates, followed by either A110 or A130 as the detection antibody.

Nunc Maxisorp Stripwells (Nunc Cat #469949) were coated with 100 μl of M110 at 3 μg/ml and incubated overnight (18–26 hours) at room temperature. The unbound material was then removed from the wells by washing four times with PBS-T. Four columns of wells then received 100 μl/well of LTA solution (Sigma Cat #2515 diluted to 1 μg/ml in PBS-T), four columns received 100 μl/well of PepG solution (10 μg/ml in PBS-T), and four columns received PBS-T alone. The wells were incubated for 30–60 minutes at room temperature and then washed four times with PBS-T. Two columns of each LTA-bound, PepG-bound, and PBS-t received 100 μl of A130, titrated in 2-fold dilutions from 5 μg/ml to 0.078 μg/ml in PBS-T with 0.1% human serum without IgG, IgA and IgM (Axell Cat BYA20341, Lot H2415). Two columns of each LTA-bound, PepG-bound, and PBS-t received A110, similarly diluted and titrated. These chimeric antibodies served as "detection" antibodies, analogous to the A130 detection antibody used in Table 18.

Following a 30–60 minute incubation, the wells were washed with PBS-T and each well received 95 μl of HRP-conjugated gamma-specific goat anti-human IgG (Zymed Cat 62-8420), diluted 1:6000 in PBS-T. After 30–60 minutes, the wells were washed with PBS-T and 100 μl of TMB substrate solution was added to each well (BioFX Cat TMBW-0100-01). The reaction was allowed to proceed for 15 minutes at room temperature in the dark and stopped by the addition of 100 μl TMB Stop Reagent to each well (BioFX Cat STPR-0100-01). The absorbance of each well was measured using a Molecular Devices Vmax microplate reader with a 450 nm filter.

Table 20 shows the results of the sandwich assay using M110 as the capture antibody, followed by PepG or LTA, and then A110 or A130 as the detection antibody. These results demonstrate again that M110 does not capture an antigen that can be bound by A130. Furthermore, this result demonstrates that the PepG preparation used in these assays does not contain appreciable levels of LTA, as capture of the PepG with anti-LTA M110 antibody does not result in sufficient captured LTA to show binding of A110 above background levels.

TABLE 20

Capture with M110, Binding of LTA or PepG, Detection with A110 or A130

| detection with A130 (µg/ml) | +LTA | +PepG | −LTA −PepG | detection with A110 (µg/ml) | +LTA | +PepG | −LTA −PepG |
|---|---|---|---|---|---|---|---|
| 5 | 0.186 | 0.197 | 0.179 | 5 | 1.237 | 0.177 | 0.174 |
| 2.5 | 0.181 | 0.197 | 0.180 | 2.5 | 1.119 | 0.172 | 0.168 |
| 1.25 | 0.209 | 0.213 | 0.190 | 1.25 | 1.036 | 0.175 | 0.172 |
| 0.625 | 0.198 | 0.223 | 0.200 | 0.625 | 0.961 | 0.189 | 0.180 |
| 0.3125 | 0.192 | 0.224 | 0.200 | 0.3125 | 0.829 | 0.190 | 0.185 |
| 0.156 | 0.192 | 0.229 | 0.199 | 0.156 | 0.688 | 0.200 | 0.197 |
| 0.078 | 0.188 | 0.217 | 0.194 | 0.078 | 0.523 | 0.187 | 0.187 |
| Buffer | 0.192 | 0.196 | 0.190 | Buffer | 0.180 | 0.179 | 0.182 |

Example 12

Human Antibodies that Bind PepG

Rather than humanizing a mouse antibody to minimize the HAMA response during treatment as described above, a skilled artisan can isolate a protective anti-PepG antibody that is fully human. There are a number of well-known alternative strategies one of ordinary skill in the art may use to produce completely human recombinant antibodies. One is the generation of antibodies using phage display technologies (50, 54). Specifically, human RNA is used to produce a cDNA library of antibody heavy and light chain fragments expressed on the surface of bacteriophage. These libraries can be used to probe against the antigen of interest (i.e., PepG) and the phage that bind, because of the antibody expressed on the surface, are then isolated. The DNA encoding the variable regions is sequenced and cloned for antibody expression.

Another method of producing human antibodies employs "humanized" mice. These transgenic mice have had their own antibody genes replaced with a portion of the human antibody gene complex so that upon inoculation with antigen, they produce human antibodies (48, 50, 51, 52, 54). The antibody producing cells that result can then be incorporated into the standard hybridoma technology for the establishment of specific monoclonal antibody producing cell lines.

Recombinant human antibodies are also produced by isolating antibody-producing B cells from human volunteers that have a robust anti-PepG response. Using fluorescence activated cell sorting (FACS) and fluorescently labeled PepG, cells producing the anti-PepG antibodies can be separated from the other cells. The RNA can then be extracted and the sequence of the reactive antibody variable regions determined (49, 53). The DNA sequence of the functional variable regions can be synthesized or cloned into mammalian expression vectors for large-scale human recombinant antibody production.

CONCLUSION

Monoclonal antibodies were raised in mice against *S. aureus* PepG, an abundant cell surface molecule on Gram-positive bacteria. One hybridoma clone, 99-110FC12 IE4, produces an IgM antibody that bound strongly in ELISA assays to PepG, but not to *S. epidermidis* strain Hay, or to LTA, another surface molecule common to Gram-positive bacteria (Example 1, Table 5).

Monoclonal antibodies were also raised against *B. subtilis* PepG. Hybridomas BB4/A4 and BB4/A5 produce IgG antibodies that bind to *B. subtilis* PepG (Example 2). The affinity of the monoclonal antibodies produced by BB4/A4, BB4/A5, 11-232.3, 11-248.2, 11-569.3, and antibody 702 PG, which is purified from hybridoma 11-232.3, were tested for binding to PepG from a number of different bacteria in an ELISA assay. MAb-BB4/A4 and MAb-BB4/A5, which were produced from the same mouse, bound strongly to PepG from *B. subtilis* and *S. epidermidis*, while MAb-11-232.3 and MAb-11-248.2 bound strongly to PepG *S. aureus* (Example 3, Table 6). These results demonstrate that monoclonal antibodies raised against PepG from one Gram positive bacteria may bind PepG from another Gram-positive bacteria, which may indicate binding to a conserved epitope on PepG.

A110, MAb-11-232.3, MAb-11-248.2, MAb-99-110FC12 IE4, and MAb-11-569.3 were tested for binding to *S. aureus* PepG in an ELISA assay. MAb-11-232.3, MAb-11-248.2, and MAb-99-110FC12 IE4, which were raised to either whole UV-killed *S. aureus* or to *S. aureus* PepG, bound strongly to *S. aureus* PepG. MAb-11-569.3 bound weakly to PepG, although it was also raised to whole UV-killed *S. aureus*, indicating that it may bind to an epitope other than PepG on the surface of the bacteria. The anti-LTA antibody, A110, did not bind to *S. aureus* PepG (Example 4, Table 7). In a similar assay to measure binding of the antibodies to *S. aureus* LTA, only A110 showed appreciable binding (Example 4, Table 8). The results demonstrate that antibodies raised to whole UV-killed *S. aureus* may in fact be specific for PepG on the surface of the bacteria.

Each of the antibodies was then tested for binding to methanol-fixed *S. epidermidis* strain Hay. A110, which was raised to *S. epidermidis* LTA, bound most strongly to methanol-fixed *S. epidermidis*. MAb-11-569.3 and MAb-11-248.2 also bound strongly to the methanol-fixed *S. epidermidis*, in spite of the fact that they were raised to UV-killed *S. aureus*. This suggests that these antibodies may bind to a conserved epitope on the surface of the two bacterial strains. MAb-11-232.3, which was also raised to UV-killed *S. aureus* bound less strongly to methanol-fixed *S. epidermidis*. Similarly, MAb-99-110FC12 IE4, which was raised against *S. aureus* PepG, did not bind methanol-fixed *S. epidermidis* (Example 4, Table 9).

Finally, A110, MAb-11-232.3, and MAb-11-569.3 were tested for binding to methanol-fixed *S. aureus*. Not surprisingly, MAb-11-232.3 and MAb-11-569.3 bound strongly, as they were raised to whole UV-killed *S. aureus*. A110 also bound to methanol-fixed *S. aureus*, although it was raised to heat-killed *S. epidermidis*, indicating that it may bind to an epitope that is conserved between the two bacteria (Example 4, Table 10).

Hybridoma 99-110FC12 IE4 supernatant was tested for opsonic activity against *S. aureus* and *S. epidermidis* in the presence of PMNs and complement, which was derived from human serum that had been depleted of antibodies to *S. aureus* and *S. epidermidis*. MAb-99-110FC12 IE4 was opsonic against *S. aureus*, but not against *S. epidermidis* (Example 5, Table 11). As discussed in the preceding paragraphs, MAb-99-110FC12 IE4 binds to *S. aureus* PepG, but not to whole *S. epidermidis*, suggesting a correlation between binding ability and opsonic activity.

MAb-11-232.2, MAb-11-569.3, MAb-11-248.2, each of which was raised to whole UV-killed *S. aureus*, as well as MAb-99-110FC12 IE4, which was raised to purified *S. aureus* PepG, and A110 were tested in a similar opsonophagocytic assay against *S. aureus* type 5. The antibodies that were raised against UV-killed *S. aureus*, MAb-11-232.2, MAb-11-569.3, and MAb-11-248.2, as well as MAb-110FC12 IE4, which was raised against *S. aureus* PepG, showed at least 75% killing of *S. aureus* in the assay. The anti-LTA antibody, A110, which was raised against LTA from *S. epidermidis*, showed only 23% killing (Example 5, Table 12). Surprisingly, although A110 bound strongly to both *S. aureus* LTA and whole methanol-fixed *S. aureus*, it was not strongly opsonic against *S. aureus*. The non-chimerized version of A110, M110, was somewhat more opsonic against *S. aureus* in a previous assay (Example 5, Table 12B). This variation, however, is likely due to assay to assay variations and dosage effects, rather than differences in activity between the chimerized and non-chimerized antibodies, because A110 retains its activity against *S. epidermidis* (Example 5, Table 13). The antibodies that were raised against *S. aureus* PepG, and against whole UV-killed *S. aureus*, on the other hand, showed strong opsonic activity against the bacteria, as was expected.

In a similar assay against *S. epidermidis* strain Hay, MAb-11-232.2, MAb-11-569.3, and MAb-11-248.2 showed at least 66% killing, while MAb-99-110FC12 IE4 showed little or no killing. A110, in contrast with the previous assay, showed at least 98% killing of *S. epidermidis* strain Hay (Example 5, Table 13). These results, and those discussed above, show a strong correlation between the ability to bind to methanol-fixed bacteria and opsonic activity against that bacteria. A110 is a notable exception, however, because it was able to bind to methanol-fixed *S. aureus*, but was not opsonic against live *S. aureus*. Furthermore, these results demonstrate that monoclonal antibodies that have been raised against UV-killed *S. aureus* can have opsonic activity against *S. epidermidis*, suggesting a conserved determinant between the two bacteria that allows a MAb raised against one to be opsonic for the other. These results also indicate that weak binding may be sufficient for opsonic activity, because MAb-11.232.3 was still somewhat opsonic against *S. epidermidis*, in spite of its poor binding to those bacteria in the methanol-fixed bacteria ELISA.

MAb-11-232.3 was tested for its ability to block nasal colonization in mice. After preincubation of *S. aureus* type 5 with MAb-11-232.3, only 3 out of 8 mice were colonized by *S. aureus*, as compared to 9 out of 9 mice in the control groups. Furthermore, of the mice that were colonized, the mice that received *S. aureus* that had been preincubated with MAb-11-232.3 had one-tenth the number of bacterial colonies as control mice (Example 6, Table 14). These results suggest that MAb-11-232.3, which binds to and is opsonic against *S. aureus*, is able to block nasal colonization by the bacteria, and is also able to reduce the number of bacteria in mice that are colonized.

Hybridoma 11-232.3 was subcloned, and the antibody produced by subclone 11-232.3 IE9, M130, was further analyzed. M130 was tested for binding to a number of different bacteria in a live bacteria ELISA assay. M130 bound to three different strains of live *S. aureus*, but did not bind to *S. hemolyticus* or *S. epidermidis* (Example 7, Table 16). These results are consistent with the methanol-fixed bacteria ELISAs, in which MAb-11-232.3 bound strongly to *S. aureus*, but weakly to *S. epidermidis*. Therefore, although MAb-11.232.3 and M130 are specific for *S. aureus*, they are broadly reactive against different strains of bacteria, as MAb-11-232.3 was still somewhat opsonic against *S. epidermidis*, in spite of its weaker binding.

The variable regions of M130 were cloned and human/mouse chimeric antibodies were produced that have the M130 variable regions and human constant regions (Examples 8 and 9). These chimeric antibodies, referred to as A130, retained the ability to bind to *S. aureus* PepG (Example 10, FIG. 7). These human/mouse chimeric antibodies are expected to have a reduced HAMA response in humans, which may be therapeutically advantageous.

Finally, sandwich assays were conducted to confirm that the anti-PepG antibodies of the invention are in fact specific for PepG, and do not bind to contaminants in PepG preparations. In the first assay, a battery of antibodies were used to capture PepG on a plate, and then A130 was used as a detection antibody to detect the captured PepG (Example 11, Table 18). As expected, antibodies that are known to bind to PepG were able to capture PepG, as detected by binding of A130 antibody. Antibodies that bind to LTA did not capture an antigen that could be detected by A130, indicating that A130 does not bind to LTA. In the second assay, anti-LTA A110 antibody was used to capture LTA on a plate, which was then detected with the same battery of antibodies as was used for capture in the first assay (Example 11, Table 19). As expected, the anti-LTA antibodies were able to detect the LTA that was captured by A110. The anti-PepG antibodies, on the other hand, were unable to detect an antigen captured by A110, suggesting that they do not bind to LTA. Finally, M110 was used to capture either LTA or PepG on a plate, and the captured antigen was then detected with either A110 or A130 (Example 11, Table 20). As expected, M110 was not able to capture an antigen from either the PepG or LTA preparations that was detectable by A130. M110 was able to capture LTA that was detectable by A110, however. Significantly, M110 was not able to capture sufficient LTA from the PepG preparation to allow measurable detection by A110, suggesting that the PepG preparation is substantially free of LTA. This level of purity in a PepG preparation has not previously been demonstrated.

Previously, it was unclear whether a monoclonal antibody could enhance phagocytosis of Gram-positive bacteria, because the polyclonal sera that were used contained many different antibodies that bound to many different epitopes on the surface of the bacteria, and the sum of this collective binding and activities may have accounted for the overall activity of the serum. Here, we demonstrate that a monoclonal antibody, which binds to a single epitope on the surface of bacteria, can be opsonic against that bacteria. We have also demonstrated that monoclonal antibodies raised against PepG can have that activity, and that those antibodies may be opsonic for a number of different types of Gram-positive bacteria.

The antibodies of the invention can block or alleviate nasal colonization. These antibodies may therefore be useful protective molecules in the fight against antibiotic-resistant Gram-positive bacterial infections.

REFERENCES

1. Atrih, Abdelmadjid; Bacher, Gerold; Allmaier, Gunter; Williamson, Michael P.; and Foster, Simon J. 1999. Analysis of Peptidoglycan Structure from Vegetative Cells of *Bacillus subtilis* 168 and Role PBP 5 in Peptidoglycan Maturation, *Journal of Bacteriology* 181: 3956–3966.
2. Bartal, Arie H.; Hirshaut, Yashar. 1987. Current Methods in Hybridoma Formation Bartal, A. H. et al. (ed.) *Methods of Hybridoma Formation*, Humana Press, Clifton, N.J.
3. Espersen, F.; Hertz, J. B.; and Hoiby, N. 1981. Cross-Reactions Between *Staphylococcus epidermis* and 23 Other Bacterial Species, *Acta Path. Microbial. Scand.*, Sect. B. 89: 253–260.
4. Fischer, Gerald W. Broadly reactive opsonic antibodies that react with common *staphylococcal* antigens, U.S. Pat. No. 5,571,511, issued Nov. 5, 1996.
5. Fleer, A.; Senders R. C.; Visser M. R.; Bijimer R. P.; Gerards L. J.; Kraaijeveld C. A.; Verhoef J. 1983. Septicemia due to coagulase-negative *staphylococci* in a neonatal intensive care unit: clinical and bacteriological features and contaminated parenteral fluids as a source of sepsis, *Pediatr. Infect. Dis.* 2: 426–431.
6. Foster, Simon J. 1992. Analysis of the Autolysins of *Bacillus subtilis* 168 during Vegetative Growth and Differentiation by Using Renaturin Polyacrylamide Gel Electrophoresis, *Journal of Bacteriology* 174: 464–470.
7. Fournier, Jean-Michel. 1991. *Staphylococcus Aureus, Vaccines and Immunotherapy*, Ch. 13, pp. 166–171.
8. Genarro, A. (ed.) 1990. *Remington's Pharmaceutical Sciences*, 18$^{th}$ Edition, Mack Publishing, Easton, Pa.
9. Hancock, I. C. 1997. Bacterial Cell Surface Carbohydrates: Structure and Assembly, *Biochem. Soc. Trans.* 25:183–187.
10. Jendeberg, Lena; Nilsson, Peter; Larsson, Antonella; Denker, Per; Uhlen, Mathias; Nilsson, Bjorn; Nygren, Per-Ake. 1997. Engineering of Fc1 and Fc3 from Human Immunoglobulin G to Analyse Subclass Specificity for Staphylococcal Protein A, *J. Immunol. Methods* 201: 25–34.
11. Kiser, Kevin B.; Cantey-Kiser, Jean M.; Lee, Jean C. 1999. Development and Characterization of a *Staphylococcus Aureus* Nasal Colonization Model in Mice, *Infection and Immunity* 67: 5001–5006.
12. Krieger, Monty; Joiner, Keith A. Method for Treating Gram Positive Septicemia, U.S. Pat. No. 5,624,904, issued Apr. 29, 1997.
13. Lee, J. C. 1996. The prospects for developing a vaccine against *Staphylococcus aureus*, *Trends in Micro.* 4: 162–66.
14. LoBuglio A. F.; Wheeler R. H.; Trang J.; Haynes A.; Rogers K.; Harvey E. B.; Sun L.; Ghrayeb J.; Khazaeli M. B. 1989. Mouse/human chimeric monoclonal antibody in man: kinetics and immune response, P.N.A.S. 86: 4220–4224.
15. Nakamura, K. et al. 1999. Uptake and Release of Budesonide from Mucoadhesive, pH-sensitive Copolymers and Their Application to Nasal Delivery. *J. Control. Release* 61:329–335.
16. Natsume, H., S. Iwata, K. Ohtak, M. Miyamoto, M. Yamaguchi, K. Hosoya, and D. Kobayashi. 1999. Screening of cationic compounds as an absorption enhancer for nasal drug delivery. *Int. J. Pharma.* 185:1–12.
17. Navarre, William Wiley and Schneewind, Olaf. 1999. Surface Proteins of Gram-Positive Bacteria and Mechanisms of Their Targeting to the Cell Wall Envelope, *Microbiology and Molecular Biology Reviews* 63: 174–229.
18. Peterson, Phillip K.; Verhoef, Jan; Sabath, L. D.; and Quie, Paul G. 1997. Effect of Protein A on Staphylococcal Opsonization, *Infection and Immunity* 15: 760–764.
19. Peterson, Phillip K.; Wilkinson, Brian J.; Kim, Youngki; Schmeling, David; and Quie, Paul G. 1978. Influence of Encapsulation on Staphylococcal Opsonization and Phagocytosis by Human Polymorphonuclear Leukocytes, *Infection and Immunity* 19: 943–949.
20. Peterson, Phillip K.; Wilkinson, Brian J.; Kim, Youngki; Schmeling, David; Douglas, Steven D.; Quie, Paul G.; and Verhoef, Jan. 1978. The Key Role of Peptidoglycan in the Opsonization of *Staphylococcus Aureus*, *The Journal of Clinical Investigation* 61: 597–609.
21. Quie, Paul G.; Hill, Harry R.; and Davis, Todd A. 1974. Defective Phagocytosis of *Staphylococci*, *Annals New York Academy of Sciences*, pp.233–243.
22. Ramkissoon-Ganorkar, C. et al. 1999. Modulating insulin-release profile from pH/thermosensivite polymeric beads through polymer molecular weight. *J. Contr. Release* 59:287–298.
23. Romero-Vivas J.; Rubio M.; Fernandez C.; Picazo J. J. 1995. Mortality associated with nosocomial bacteremia due to methicillin-resistant *Staphylococcus aureus*, *Clin. Infect. Dis.* 21: 1417–23.
24. Salton, M. R. J. 1994. The Bacterial Cell Envelope—A Historical Perspective, in J.-M. Ghuyson and R. Hakenbeck (ed.), *Bacterial Cell Wall*, Elsevier Science B V, Amsterdam, pp. 1–22.
25. Sambrook, Joseph; Russell, David W. 1989. *Molecular Cloning: A Laboratory Manual*, 2$^{nd}$ Ed., Cold Spring Harbor Press, Cold Spring Harbor, N.Y.
26. Schwab, U. E., A. E. Wold, J. L. Carson, M. W. Leigh, P.-W. Cheng, P. H. Gilligan and T. F. Boat. 1993. Increased adherence of *Staphylococcus aureus* from cystic fibrosis lungs to airway epithelial cells. *Am. Rev. Respir. Dis.* 148:365–369.
27. Shockman, Gerald D.; Jackson, Dianne E.; Wong, William. Monoclonal antibodies to Peptidoglycan and Methods of Preparing Same, U.S. Pat. No. 4,596,769, issued Jun. 24, 1986.
28. Shulman, M.; Wilde, C. D.; Kohler, G. 1978. A Better Cell Line for Making Hybridomas Secreting Specific Antibodies, *Nature* 276: 269–270.
29. Soto, N., A. Vaghjimal, A. Stahl-Avicolli, J. Protic, L. Lutwick and E. Chapnick. 1999. Bacitracin versus mupirocin for *Staphylococcus aureus* nasal colonization. *Infect. Cont. Hosp. Epidem.* 20: 351–353.
30. Suzuki, Y. and Y. Makino. 1999. Mucosal drug delivery using cellulose derivative as a functional polymer. *J. Control. Release.* 62:101–107.
31. Timmerman C. P.; Besnier J. M.; De Graaf L.; Torensma R.; Verkley A. J.; Fleer A.; Verhoef J. 1991. Characterisation and functional aspects of monoclonal antibodies specific for surface proteins of coagulase-negative *staphylococci*, *J. Med. Micro.* 35: 65–71.
32. Tomasz, Alexander. 2000. The Staphylococcal Cell Wall, in V. A. Fischetti et al. (ed.) *Gram-Positive Pathogens*, Ch. 36, pp. 351–355.
33. Verbrugh, Henri A.; Peters, Roel; Rozenberg-Arska, Maja; Peterson, Phillip K.; and Verhoef, January 1981. Antibodies to Cell Wall Peptidoglycan of *Staphylococcus aureus* in Patients with Serious Staphylococcal Infections, *The Journal of Infectious Disease* 144: 1–9.

34. Verbrugh, Henri A.; Van Dijk, Willemien C.; Peters, Roel; Van Erne, Marijke E.; Daha, Mohamed R.; Peterson, Phillip K. and Verhoeff, January 1980. Opsonic Recognition of *Staphylococci* Mediated by Cell Wall Peptidoglycan: Antibody-Independent Activation of Human Complement and Opsonic Activity of Peptidoglycan Antibodies, *The Journal of Immunology* 124: 1167–1173.
35. Waldvogel, Francis A. 1990. *Staphylococcus Aureus* (Including toxic Shock Syndrome), Mandell, G. L. et al. (ed.), *Principles and Practices of Infectious Diseases, Third Edition*, Churchill Livingstone, Philadelphia, Pa., pp. 1489–1510.
36. Waldvogel, Francis A. 2000. *Staphylococcus Aureus* (Including toxic Shock Syndrome), Mandell, G. L. et al. (ed.) *Principles and Practice of Infectious Diseases, Fifth Edition*, Churchill Livingstone, Philadelphia, Pa., pp. 1760–1775.
37. Merkus, F. W., J. C. Verhoef, N. G. Schipper, and E. Marttin. 1999. Cyclodextrins in nasal drug delivery. *Advan. Drug Deliv. Rev.* 36: 41–57.
38. Kengatharan, K. M., De Kimpe, S., Robson, C., Foster, S. J. & Thiemermann, C. 1998. Mechanism of Gram-positive shock: Identification of peptidoglycan and lipoteichoic acid moieties essential in the induction of nitric oxide synthase, shock and multiple organ failure. *Journal of Experimental Medicine* 188: 305–315.
39. Foster, S. J. 1993. Molecular analysis of three major wall-associated proteins of *Bacillus subtilis* 168: evidence for the processing the product of a gene encoding a 258 kDa precursor two-domain ligand-binding protein. *Molecular Microbiology* 8: 299–310.
40. Devereux, J., Haeberli, P. & Smithies, O. 1984. A comprehensive set of sequence analysis programs for the VAX. Nucl. Acids Res. 12: 387–395.
41. Needleman, S. B. & Wunsch, C. D. 1970. A general method applicable to the search for similarities in the amino acid sequence of two proteins. J. Mol. Biol. 48: 443–453.
42. Smith, T. F. & Waterman, M. S. 1981. Comparison of biosequences. Adv. Appl. Math 2: 482–489.
43. Gribskov, M. & Burgess, R. R. 1986. Sigma factors from *E. coli, B. subtilis*, phage SP01, and phage T4 are homologous proteins. 14: 6745–6763.
44. Schwartz, R. M. & Dayhoff, M. O. 1979. "Matrices for detecting distant relationships", pp. 353–358 in: Atlas of Protein Sequence and Structure. National Biomedical Research Foundation.
45. Ausubel et al. (ed.) 1989. Current Protocols in Molecular Biology, John Wiley & Sons.
46. Borrebaeck, Carl A. K. 1995. *Antibody Engineering*, 2nd Ed., Oxford University Press, NY.
47. Harlow, Ed; Lane, David. 1988. Antibodies: A Laboratory Manual, Cold Spring Harbor Press, Cold Spring Harbor, N.Y.
48. Green, L. L., M. C. Hardy, et al. (1994). "Antigen-specific human monoclonal antibodies from mice engineered with human Ig heavy and light chain YACs." Nat Genet 7(1): 13–21.
49. Kantor, A. B., C. E. Merrill, et al. (1995). "Development of the antibody repertoire as revealed by single-cell PCR of FACS-sorted B-cell subsets." Ann N Y Acad Sci 764: 224–7.
50. Low, N. M., P. H. Holliger, et al. (1996). "Mimicking somatic hypermutation: affinity maturation of antibodies displayed on bacteriophage using a bacterial mutator strain." J Mol Biol 260(3): 359–68.
51. Wagner, S. D., A. V. Popov, et al. (1994). "The diversity of antigen-specific monoclonal antibodies from transgenic mice bearing human immunoglobulin gene miniloci." Eur J Immunol 24(11): 2672–81.
52. Wagner, S. D., G. T. Williams, et al. (1994). "Antibodies generated from human immunoglobulin miniloci in transgenic mice." Nucleic Acids Res 22(8): 1389–93.
53. Wang, X. and B. D. Stollar (2000). "Human immunoglobulin variable region gene analysis by single cell RT-PCR." J Immunol Methods 244(1–2): 217–25.
54. Winter, G., A. D. Griffiths, et al. (1994). "Making antibodies by phage display technology." Annu Rev Immunol 12: 433–55.

Having now fully described the invention, it will be appreciated by those skilled in the art that the invention can be performed within a range of equivalents and conditions without departing from the spirit and scope of the invention and without undue experimentation. In addition, while the invention has been described in light of certain embodiments and examples, the inventors believe that it is capable of further modifications. This application is intended to cover any variations, uses, or adaptations of the invention which follow the general principles set forth above.

The specification includes recitation to the literature and those literature references are herein specifically incorporated by reference.

What is claimed is:

1. A composition comprising a therapeutically effective amount of a monoclonal antibody (MAb), or an antigen-binding portion thereof, that specifically binds to peptidoglycan (PepG), wherein the MAb is produced by the hybridoma deposited with the ATCC under Accession Number PTA-3659 and a pharmaceutically acceptable carrier.

2. A composition comprising a therapeutically effective amount of a monoclonal antibody (MAb), or an antigen-binding portion thereof, that specifically binds to peptidoglycan (PepG), wherein the comprises a light chain variable region comprising the amino acid sequence set forth in SEQ ID NO:1 and a heavy chain variable region comprising the amino acid sequence set forth in SEQ ID NO:3 and a pharmaceutically acceptable carrier.

3. The composition of claim 1 or 2, wherein administration of the composition to a patient reduces the number of Gram-positive bacteria in the patient.

4. The composition of claim 1 or 2, wherein the MAb, or antigen-binding portion thereof, specifically binds to PepG at a level at least two-fold greater than a control in an ELISA.

5. The composition of claim 1 or 2, wherein the MAb, or antigen-binding portion thereof, enhances antibacterial opsonophagocytosis of Gram-positive bacteria by at least 50% compared to a control.

6. The composition of claim 1 or 2, further comprising an additional MAb, or a antigen-binding portion thereof, that specifically binds to lipoteichoic acid (LTA) of Gram-positive bacteria.

7. The composition of claim 1 or 2, wherein the MAb, or antigen-binding portion thereof, blocks colonization by Gram-positive bacteria upon instillation into the nares of a patient.

8. The composition of claim 1 or 2, wherein the MAb, or antigen-binding portion thereof, is selected from the group consisting of a full length chimeric Mab and a full length humanized MAb or an antigen binding portion thereof.

9. The composition of claim 1 or 2, wherein the MAb or antigen-binding portion thereof comprises a modified Fc portion, wherein said modification reduces nonspecific binding of the MAb via the Fc portion.

10. The composition of claim 1 or 2, wherein the MAb, or antigen-binding portion thereof, is an antigen binding fragment selected from the group consisting of a Fab, Fab', F(ab')$_2$, Fv, SFv, and scFv fragment.

11. The composition of claim 1 or 2, further comprising at least one antistaphylococcal drug.

12. A hybridoma cell line deposited at the ATCC under accession no. PTA-3659.

* * * * *

SEQUENCE LISTING

```
<160> NUMBER OF SEQ ID NOS: 12

<210> SEQ ID NO 1
<211> LENGTH: 112
<212> TYPE: PRT
<213> ORGANISM: Artificial Sequence
<220> FEATURE:
<223> OTHER INFORMATION: Description of Artificial Sequence: Synthetic
      M130 light chain antibody

<400> SEQUENCE: 1

Asp Ile Lys Met Thr Gln Ser Pro Leu Thr Leu Ser Val Thr Ile Gly
 1               5                   10                  15
```

```
Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ala Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Leu Thr Phe Gly Ala Gly Thr Lys Leu Glu Leu Lys
            100                 105                 110

<210> SEQ ID NO 2
<211> LENGTH: 336
<212> TYPE: DNA
<213> ORGANISM: Artificial Sequence
<220> FEATURE:
<221> NAME/KEY: CDS
<222> LOCATION: (1)..(336)
<220> FEATURE:
<223> OTHER INFORMATION: Description of Artificial Sequence: Synthetic
      DNA encoding M130 light chain antibody

<400> SEQUENCE: 2 gat att aag atg acc cag tct cca ctc act ttg tcg gtt acc att gga      48
Asp Ile Lys Met Thr Gln Ser Pro Leu Thr Leu Ser Val Thr Ile Gly
  1               5                  10                  15 caa cca gcc tcc atc tct tgc aag tca agt cag agc ctc tta gat agt      96
Gln Pro Ala Ser Ile Ser Cys Lys Ser Ser Gln Ser Leu Leu Asp Ser
             20                  25                  30 gat gga aag aca tat ttg aat tgg ttg tta cag cgg cca ggc cag tct     144
Asp Gly Lys Thr Tyr Leu Asn Trp Leu Leu Gln Arg Pro Gly Gln Ser
         35                  40                  45 cca aag cgc cta atc tat ctg gtg tct aaa ctg gac tct gga gtc cct     192
Pro Lys Arg Leu Ile Tyr Leu Val Ser Lys Leu Asp Ser Gly Val Pro
     50                  55                  60 gac agg ttc gct ggc agt gga tca ggg aca gat ttc aca ctg aaa atc     240
Asp Arg Phe Ala Gly Ser Gly Ser Gly Thr Asp Phe Thr Leu Lys Ile
 65                  70                  75                  80 agc aga gtg gag gct gag gat ttg gga gtt tat tat tgc tgg caa ggt     288
Ser Arg Val Glu Ala Glu Asp Leu Gly Val Tyr Tyr Cys Trp Gln Gly
                 85                  90                  95 aca cat ttt cct ctc acg ttc ggt gct ggg acc aag ttg gaa ctg aaa     336
Thr His Phe Pro Leu Thr Phe Gly Ala Gly Thr Lys Leu Glu Leu Lys
            100                 105                 110

<210> SEQ ID NO 3
<211> LENGTH: 119
<212> TYPE: PRT
<213> ORGANISM: Artificial Sequence
<220> FEATURE:
<223> OTHER INFORMATION: Description of Artificial Sequence: Synthetic
      M130 heavy chain antibody

<400> SEQUENCE: 3

Gln Val Gln Leu Gln Gln Ser Gly Pro Gly Ile Leu Gln Pro Ser Gln
  1               5                  10                  15

Thr Leu Ser Leu Thr Cys Ser Phe Ser Gly Phe Ser Leu Ser Thr Ser
             20                  25                  30

Gly Met Ser Val Ser Trp Ile Arg Gln Pro Ser Gly Lys Gly Leu Glu
         35                  40                  45
```

```
Trp Leu Ala His Ile Phe Trp Asp Asp Asp Lys Arg Tyr Asn Pro Ser
    50                  55                  60

Leu Lys Ser Arg Leu Thr Val Ser Lys Asp Thr Ser Ser Asn Gln Val
65                  70                  75                  80

Phe Leu Lys Ile Thr Ser Val Gly Thr Ala Asp Thr Ala Thr Tyr Tyr
                85                  90                  95

Cys Ala Arg Asn Tyr Asp Tyr Asp Trp Phe Val Tyr Trp Gly Gln Gly
            100                 105                 110

Thr Leu Val Thr Val Ser Ala
        115

<210> SEQ ID NO 4
<211> LENGTH: 357
<212> TYPE: DNA
<213> ORGANISM: Artificial Sequence
<220> FEATURE:
<221> NAME/KEY: CDS
<222> LOCATION: (1)..(357)
<220> FEATURE:
<223> OTHER INFORMATION: Description of Artificial Sequence: Synthetic
      DNA encoding M130 heavy chain antibody

<400> SEQUENCE: 4 cag gtt cag ctg cag cag tct ggc cct ggg ata ttg cag ccc tcc cag      48
Gln Val Gln Leu Gln Gln Ser Gly Pro Gly Ile Leu Gln Pro Ser Gln
 1               5                  10                  15 acc ctc agt ctg act tgt tct ttc tct ggg ttt tca ctg agc act tct      96
Thr Leu Ser Leu Thr Cys Ser Phe Ser Gly Phe Ser Leu Ser Thr Ser
             20                  25                  30 ggt atg agt gtg agc tgg att cgt cag cct tca gga aag ggt ctg gag     144
Gly Met Ser Val Ser Trp Ile Arg Gln Pro Ser Gly Lys Gly Leu Glu
         35                  40                  45 tgg ctg gct cac att ttc tgg gat gat gac aag cgc tat aac cca tcc     192
Trp Leu Ala His Ile Phe Trp Asp Asp Asp Lys Arg Tyr Asn Pro Ser
    50                  55                  60 ctg aag agc cga ctc aca gtc tcc aag gat acc tcc agc aac cag gtc     240
Leu Lys Ser Arg Leu Thr Val Ser Lys Asp Thr Ser Ser Asn Gln Val
65                  70                  75                  80 ttc ctc aag atc acc agt gtg ggc act gca gat act gcc aca tac tac     288
Phe Leu Lys Ile Thr Ser Val Gly Thr Ala Asp Thr Ala Thr Tyr Tyr
                85                  90                  95 tgt gct cga aac tat gat tac gac tgg ttt gtt tac tgg ggc caa ggg     336
Cys Ala Arg Asn Tyr Asp Tyr Asp Trp Phe Val Tyr Trp Gly Gln Gly
            100                 105                 110 act ctg gtc act gtc tct gca                                         357
Thr Leu Val Thr Val Ser Ala
        115

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 5
tgttttcgta cgtcttgtcc caggtbcarc tkmarsartc                          40

<210> SEQ ID NO 6
<211> LENGTH: 32
<212> TYPE: DNA
<213> ORGANISM: Artificial Sequence
```

```
<220> FEATURE:
<223> OTHER INFORMATION: Description of Artificial Sequence: Primer

<400> SEQUENCE: 6
taccgtaccg gtgayatyma gatgacmcag wc                            32

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 7
taccgtaccg gtsaaattgw kctsacycag tc                            32

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 8
gcacctccag atgttaactg ctc                                      23

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 9
ctggacaggg mtccakagtt cc                                       22

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 10
ataggattcg aaaagtgtac ttmcgtttca gytccarc                      38

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 11
tgttttcgta cgtcttgtcc cag                                      23

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 12
ttttctgaat tctgcagaga cagtgaccag agtcc                         35
```